United States Patent [19]
Bentsen

[11] Patent Number: 5,518,694
[45] Date of Patent: May 21, 1996

[54] EMISSION QUENCHING SENSORS

[75] Inventor: James G. Bentsen, North St. Paul, Minn.

[73] Assignee: Minnesota Mining and Manufacturing Company, St. Paul, Minn.

[21] Appl. No.: 454,055

[22] Filed: May 30, 1995

Related U.S. Application Data

[62] Division of Ser. No. 136,967, Oct. 14, 1993, Pat. No. 5,462,879.

[51] Int. Cl.$^6$ .................................................. G01N 21/64
[52] U.S. Cl. ...................... 422/82.08; 422/91; 250/458.1
[58] Field of Search ........................... 422/82.07, 82.08, 422/79, 91; 436/172; 250/458.1

[56] References Cited

U.S. PATENT DOCUMENTS

| | | | |
|---|---|---|---|
| Re. 31,879 | 5/1985 | Lubbers et al. | 436/133 |
| 4,374,328 | 2/1983 | Tekippe et al. | 250/458.1 |
| 4,716,363 | 12/1987 | Dukes et al. | 324/77 R |
| 4,845,368 | 7/1989 | Demas et al. | 250/459.1 |
| 5,030,420 | 7/1991 | Bacon et al. | 422/82.07 |
| 5,057,277 | 10/1991 | Mauze et al. | 422/56 |
| 5,094,958 | 3/1992 | Klainer et al. | 436/172 |
| 5,184,618 | 2/1993 | Wider et al. | 128/634 |

FOREIGN PATENT DOCUMENTS

| | | |
|---|---|---|
| 2000303 | 4/1990 | Canada . |
| 0442295A2 | 1/1991 | European Pat. Off. . |
| 0442276A1 | 1/1991 | European Pat. Off. . |
| WO92/10739 | 1/1991 | WIPO . |
| WO92/05541 | 4/1992 | WIPO . |
| WO92/12424 | 7/1992 | WIPO . |

OTHER PUBLICATIONS

E. R. Carraway, J. N. Demas, B. A. DeGraff and J. R. Bacon, "Photophysics and Photochemistry of Oxygen Sensors Based on Luminescent Transition–Metal Complexes", *Anal. Chem.*, vol. 63, No. 4, pp. 337–342.
Chu Ngi Ho, Gabor Patonay and Isiah M. Warner, "Bioanalytical application of fluorescence quenching", *Trends in Analytical Chemistry*, vol. 5, No. 2, 1986, pp. 37–43.
P. M. Gewehr and D. T. Delpy, "Optical oxygen sensor based on phosphorescence lifetime quenching and employing a polymer immobilised metalloporphyrin probe", *Medical & Biological Engineering & Computing*, Jan. 1993, pp. 2–10.
Gerhard Holst et al., 02–flux–optode for medical application, Proc. SPIE–Int. Soc. Opt. Eng., v. 1885, Proceedings of Advances in Fluorescence Sensing Tech. 1993, pp. 216–227.
Maria Moreno–Bondi et al., "Oxygen Optrode for Use in a Fiber–Optic Glucose Biosensor", Analytical Chemistry, vol. 62, No. 21, pp. 2377–2380, Nov. 1, 1990.

(List continued on next page.)

*Primary Examiner*—Jeffrey R. Snay
*Attorney, Agent, or Firm*—Gary L. Griswold; Walter N. Kirn; F. Andrew Ubel

[57] ABSTRACT

The present invention relates to a sensing instrument and method for measuring the concentration of an analyte. The sensing instrument includes: a sensing element including at least a first emissive indicator characterized by a bimolecular quenching rate constant $k_q$, one or more fluorescence lifetimes $\tau_o$ above a lowest lifetime $\tau_{oL}$, and capable of emitting analyte concentration dependent signals when exposed to an excitation signal in the presence of quencher; an excitation system which provides an amplitude modulated excitation signal at one or more radial modulation frequencies $\omega$; a detector; and a processor. The processor univariantly processes the detected signals and provides output signals representative of analyte concentration. The sensing element and/or excitation system are configured to enable the instrument to operate sufficiently within the condition $[(k_q[Q])^2+\omega^2]\tau_o^2 \gg 1+2k_q\tau_o[Q]$ such that a slope of the relationship between the concentration dependent parameter and analyte concentration is independent of $\tau_o$ variability and/or heterogeneity for all analyte concentrations within the operating range and for all lifetimes $\tau_o$ greater than $\tau_{oL}$.

28 Claims, 22 Drawing Sheets

OTHER PUBLICATIONS

Otto Wolfbeis, *Fiber Optic Chemical Sensors and Biosensors,* vol. II, CRC Press, pp. 19–53.

J. Lackowicz, "Measurement of Flurorescence Lifetimes", Principles of Fluorescence Spectroscopy, 1986, pp. 51–56, 76–76, 79–86, 257–265, 383–388.

J. Demas et al., "Elimination of Quenching Effects in Luminescence Spectrometry by Phase Resolution", Analytical Chemistry, vol. 58, No. 8, pp. 1717–1721, Jul. 1986.

J. Demas, "Error Analysis of Phase Resolution Methods for Elimination of Quenching Effects in Luminescence Spectroscopy", SPIE vol. 910, Flurorescence Detection II, pp. 162–167, 1988.

EMISSION QUENCHING SENSORS

This is a division of application Ser. No. 08/136,967 filed Oct. 14, 1993, now U.S. Pat. No. 5,462,879.

FIELD OF THE INVENTION

The present invention relates generally to sensors for measuring the concentration of an analyte of interest in a medium. In particular, the present invention is a dynamic emission (e.g., fluorescence) quenching/phase-modulation based sensor for the monitoring of blood gas (e.g., oxygen, ionized hydrogen, ionized potassium and carbon dioxide) concentrations.

BACKGROUND OF THE INVENTION

Dynamic phase-modulation, fluorescence-based sensors are generally known. Instruments of this type are, for example, being developed or proposed for use in hospitals to monitor the concentration of gases such as oxygen, ionized hydrogen and carbon dioxide within the blood of patients. The substance of interest (e.g., oxygen) is known as the analyte.

A known property of fluorescent and photoluminescent substances referred to as fluorophores is that they absorb energy and are driven from their ground state energy level to an excited state energy level in response to the application of energy from a light source. The fluorophores are unstable in their excited states, and fluoresce (radiative decay) or give off excess thermal energy (non-radiative decay) as they return to their ground state. The fluorescence lifetime, $\tau$, represents the average amount of time the fluorophore remains in its excited state prior to returning to the ground state. The fluorescence intensity, $I$, represents the intensity of the emission given off by the fluorophore as it returns to the ground state.

When a fluorophore in a sensing element is photoexcited in the presence of another diffusing substance known as a quencher, $Q$, collisional interactions between the excited state and the quencher introduce a new mechanism for non-radiative decay, resulting in a decrease in both the fluorescence intensity and excited state lifetime. This process is known as dynamic fluorescence quenching. Furthermore, the amount by which the intensity and lifetime decrease from the respective intensity, $I_o$, and lifetime, $\tau_o$, in the absence of quencher is directly related to the quantity of the quencher, $[Q]$, present in the sensing element to which the fluorophore is exposed while fluorescing. The relationship between the fluorescence intensities and lifetimes in the absence and presence of quencher is described by the Stern-Volmer equation:

$$I_o/I = \tau_o/\tau = 1 + k_q \tau_o [Q]$$

where:

$I_o$ is the fluorescence intensity in the absence of quencher;

$I$ is the fluorescence intensity in the presence of quencher;

$\tau_o$ is the excited state lifetime in the absence of quencher;

$\tau$ is the lifetime of the fluorophore in the presence of quencher;

$k_q$ is the bimolecular quenching rate constant in the sensing element; and $[Q]$ is the concentration of the quencher in the sensing element.

Measurements of intensity or lifetime can be used to determine the concentration of a quencher in a sensing element, for example oxygen in a sensor for blood oxygen determination. The oxygen concentration in the sensing element, $[O_2]$, can be related to the oxygen partial pressure in the blood stream, $P_{O2}$, by a solubility constant, $a$. The general form of the Stern-Volmer equation therefore becomes:

$$I_o/I = \tau_o/\tau = 1 + a k_q \tau_o P_{O2} = 1 + K_{SV} P_{O2}$$

where:

$K_{SV} = a k_q \tau_o$;

$a = [O_2]/P_{O2}$ $[O_2]$ is the concentration of oxygen in the sensing element and;

$P_{O2}$ is the partial pressure of oxygen in the medium being sensed.

Oxygen is often both the analyte and fluorescence quencher for the sensing element, although this is not and need not always be the case. The fluorescence quencher and analyte of interest may be different substances, but the concentration of the analyte of interest is related to the quencher concentration by a known relationship. For example, the Moreno-Bondi et al. article *Oxygen Optrode for Use in a Fiber-Optic Glucose Biosensor*, Analytical Chemistry, Vol. 62, No. 21, (Nov. 1, 1990) describes a glucose sensor based on glucose dependent consumption of oxygen catalyzed by the enzyme glucose oxidase. The glucose oxidase is immobilized onto the surface of an oxygen sensing element. As the concentration of glucose in the external medium increases, more oxygen is consumed within the sensing element, resulting in a change in the dynamic quenching of the fluorescence by oxygen. The analyte concentration is therefore computed as a function of the quencher concentration actually measured by the instrument.

For purposes of this patent document, the term "quencher" is used to refer to the actual fluorescence quenching substance, whether this quencher is the analyte of interest or another substance related to the analyte of interest by a known relationship. It is to be understood that the concentration of the analyte of interest can be determined on the basis of the measured concentration of the quencher and the known relationship between the analyte and quencher.

A well recognized advantage of determining the fluorescence lifetime in optical sensing applications is that it is insensitive to dye concentration, optical coupling efficiencies and lamp variations.

Phase-modulation fluorescence spectroscopy is a known method for determining the lifetime, $\tau$, of a fluorophore. During the phase-modulation method the medium containing the analyte is excited by a light beam or other excitation signal that is preferably sinusoidally amplitude modulated at a radial frequency $\omega = 2\pi f$, where f is the frequency in cycles per second. The fluorescence emission from the fluorophore is a forced response to this excitation signal, and is therefore amplitude modulated at the same radial frequency $\omega$ as the excitation signal. However, because of the finite lifetime of the fluorophore in the excited state, the emission is phase shifted by an angle $\Theta$ with respect to the excitation signal. Furthermore, the amplitude or intensity of the emission is less modulated (demodulated) by an amount m with respect to the excitation signal. The lifetime of the fluorophore can be calculated in a known manner from measurements of the phase shift ($\tan \Theta = \omega \tau$) and demodulation factor ($m = (1 + \omega^2 \tau^2)^{-1/2}$).

Known phase-modulation, fluorescence-based sensing instruments such as those described in the Dukes et al. U.S. Pat. No. 4,716,363 and the Barnes et al. Canadian Patent Application 2,000,303 make use of the phase-modulation technique described above (and are operated "univariantly" as herein described) to measure the concentrations of analyte such as the partial pressure of oxygen, in a medium such as blood. These instruments include an optical fiber sensing element which is connected at the proximal end to both an optical excitation system and an optical detector. The distal end or tip of the optical fiber includes a polymer matrix which is permeable to the quencher and includes one or more fluorescable indicator components in the form of dyes. For in-vivo sensors, the sensing element is configured in the form of a probe or catheter insertable into a blood vessel of a patient to provide on-line monitoring of the oxygen concentration.

In phase modulation fluorescence spectroscopy the modulation frequency is typically chosen such that $\omega\tau \approx 1$ within the range of analyte concentration of interest. This corresponds to a phase angle near 45 degrees, where a calculation of the lifetime is least sensitive to small errors in the measured phase shift and measured demodulation ratio. The Holst et al. article *Oxygen-Flux-Optode for Medical Application*, Proc. SPIE-Int. Soc. Opt. Eng., V.1885 (Proceedings of Advances in Fluorescence Sensing Technology, 1993) pages 216–227, and Bacon et al. U.S. Pat. No. 5,030,420 describe oxygen sensors in which the phase shift is measured as a function of oxygen concentration at a fixed modulation frequency. The phase information is used to determine the fluorescence lifetime as a function of oxygen concentration. The Holst et al. article describes a sensor for which the excited state lifetime of the fluorophore in the absence of quencher is 205 nsec, from which they determine an optimum modulation frequency $f_{opt}=777$ kHz ($\omega\tau \approx 1$). For similar reasons, "univariant" sensing instruments are typically configured in such a manner that $\omega\tau \approx 1$ or $\theta \approx 45°$ over the concentration range of interest. For example, the Dukes et al. U.S. Pat. No. 4,716,363 describes a feedback system which provides the modulation frequency required to give a constant phase shift of about 45 degrees. The resulting frequency is used to determine the excited state lifetime as a function of analyte concentration. Dukes et al. suggests that the constant phase angle approach offers an advantage in that $\omega\tau = 1$ for all analyte concentrations of interest.

As discussed by Wolfbeis in the book *Fiber Optic Chemical Sensors and Biosensors*, Vol. II, CRC Press 1991 and taught by Mauze et al. in U.S. Pat. No. 5,057,277, when using intensity or lifetime measurements to determine analyte concentration, too large a Stern-Volmer quenching constant $K=ak_q\tau_o$ can be undesirable. In particular, when the quenching constant is too large, relatively large changes in lifetime and intensity occur over a narrow range of analyte concentrations. At larger analyte concentrations of interest, analyte dependent changes in the fluorescence intensity and lifetime become undesirably small. These considerations are relevant, for example, in the proper design of a sensor for monitoring oxygen partial pressure in blood, where accuracy is desired over the range of $P_{O2}$=40–120 mm mercury, more preferably over the range of $P_{O2}$=40– 200 mm mercury. A minimum accuracy of about 3 mm (about 2%) is typically required over this range.

When configured for insertion into the body of a patient, the sensing element can be required to be as small as 125 μm in diameter. The amount of luminescent dye that can be accommodated on the tip of the sensing element is therefore limited, resulting in a relatively low fluorescent signal. This problem can be partially countered by increasing the dye loading and/or photon flux. Unfortunately, dyes suitable for fluorescence quenching sensors are often subject to dye aggregation and photobleaching. Aggregation and/or photobleaching often cause the indicator components in the dye to exhibit a number of different lifetimes $\tau_o$, i.e., heterogeneous lifetimes. For any given sensor, the heterogeneous lifetimes often vary with aging and/or photodegradation. Manufacturing process variables can also result in variable lifetimes from sensor to sensor.

Calibration plots based on a measurement of the excited state lifetime will necessarily vary with changes in $\tau_o$, regardless of the method used to determine the lifetimes. Typically, two point sensor calibration and recalibration procedures are required. The initial calibration is typically performed following the assembly of the sensor or immediately prior to use. Recalibration is often required while the sensor is in use to maintain measurement accuracy. Two point, calibration procedures involve the use of two calibrants, each having known analyte concentrations. The calibrants will typically have known analyte concentrations close to the maximum and minimum concentrations of the range over which measurements are taken. During two point calibration procedures, the sensing element is alternately exposed to the two calibrants, and the slope and intercept of a calibration plot is determined so that the sensor can provide accurate analyte concentration readings. In effect, two point calibration involves adjusting the slope and intercept of the calibration data, as represented by the lookup table data or mathematical equation stored in memory of the sensor processor, until the relationship characterized by the data extends through the points corresponding to those of the known calibrants.

Since two point calibration procedures require the sensing element to be exposed to two calibrants, both in-vivo and ex-vivo sensors must be removed from the a-line circuit of arterially catheterized patients for recalibration. However, this is not acceptable procedure in most clinical situations since it can compromise the patient by, for example, increasing the risk of infection. Two point calibration procedures are also relatively time consuming.

It is evident that there is a continuing need for improved phase-modulation, fluorescence-based sensing instruments. In particular, there is a need for sensors of this type having calibration plots with slopes or slopes and intercepts that are insensitive to drift and instability caused by heterogeneous lifetimes and other variations in lifetime. A sensor capable of being characterized by a calibration plot having slopes which are insensitive to $\tau_o$ variability would have the capability of being calibrated with the use of only one calibrant having a known analyte concentration. Slopes would not depend on $\tau_o$ variability associated with unwanted dye aggregation during sensor manufacture. Furthermore, any differential photodegradation of the larger $\tau_o$ species in a sensor would give rise to a change in the intercept, but not the slope of the calibration plot. Such a sensor capable of single point calibration would increase the commercial acceptance of in-vivo blood gas monitoring since it would enable in-vivo recalibration.

SUMMARY OF THE INVENTION

The present invention is a phase-modulation, fluorescence-based sensing instrument for measuring the concentration of an analyte. The instrument can be configured to permit accurate single point in-vivo or ex-vivo recalibration.

The sensing instrument includes a sensing element configured for exposure to a quencher (i.e., the analyte of interest or a substance related to the analyte of interest) and including at least a first emissive indicator characterized by a bimolecular quenching rate constant $k_q$ for the quencher, one or more fluorescence lifetimes $\tau_o$ above a lowest lifetime $\tau_{oL}$, and capable of emitting analyte concentration dependent signal(s) having a concentration dependent parameter which varies as a function of analyte concentration when exposed to an excitation signal in the presence of quencher. An excitation system coupled to the sensing element provides an amplitude modulated excitation signal at one or more radial modulation frequencies ω. The excitation signal, for example, can be in the form of a sine wave or alternatively in the form of a more complex waveform such as a square wave defined by a fundamental modulation frequency ω and higher harmonics of ω. A detector coupled to the sensing element detects the analyte concentration dependent signal(s) and provides detected signal(s). A processor, preferably including memory for storing information characterizing a calibration relationship between analyte concentration and the concentration dependent parameter is coupled to the detector. The processor univariantly processes the detected signal(s) to derive the concentration dependent parameter, and provides output signal(s) representative of analyte concentration as a function of the derived concentration dependent parameter and the stored information.

The sensing element and/or excitation system are configured to enable the instrument to operate sufficiently within the condition $[(k_q[Q])^2+\omega^2]\tau_o^2 \gg 1+2k_q\tau_o[Q]$ such that a slope of the relationship between the concentration dependent parameter and analyte concentration is independent of $\tau_o$ variability and/or heterogeneity for all analyte concentrations within the operating range and for all lifetimes $\tau_o$ greater than $\tau_{oL}$. When configured in this manner the calibration slope is independent of $\tau_o$ variability and/or heterogeneity. The sensor can therefore be recalibrated by modifying the stored calibration information characterizing the intercept, but not the slope, of the relationship in response to sensing element exposure to one calibration analyte of a known concentration.

Preferably, the sensing element and/or excitation system are configured to enable the instrument to operate sufficiently within the condition $[(k_q[Q])^2+\omega^2]\tau_o^2 > 4[1+2k_q\tau_o[Q]]$. More preferably, the sensing element and/or excitation system are configured to enable the instrument to operate sufficiently within the condition $[(k_q[Q])^2+\omega^2]\tau_o^2 > 6[1+2k_q\tau_o[Q]]$. Most preferably, the sensing element and/or excitation system are configured to enable the instrument to operate sufficiently within the condition $[(k_q[Q])^2+\omega^2]\tau_o^2 > 10[1+2k_q\tau_o[Q]]$.

In one embodiment the sensing instrument includes an excitation system for providing the excitation signal at high modulation frequencies enabling the instrument to operate within the condition $\omega\tau_o > 10$ for all analyte concentrations within the operating range and for all lifetimes $\tau_o$ greater than $\tau_{oL}$. In another embodiment the sensing element is characterized by a sufficiently large solubility and/or diffusivity to enable the instrument to operate under the condition $k_q\tau_o[Q] > 20$ for all analyte concentrations within the operating range and for all lifetimes $\tau_o$ greater than $\tau_{oL}$.

In another embodiment of the sensing instrument the sensing element and/or excitation system are configured to enable the instrument to operate sufficiently within the conditions $[(k_q[Q])^2+\omega^2]\tau_o^2 \gg 1+2k_q\tau_o[Q]$ and $k_q\tau_o[Q] > 9$ such that both slope and intercept of the relationship between the concentration dependent parameter and analyte concentration is independent of $\tau_o$ variability for all analyte concentrations within the operating range and for all lifetimes $\tau_o$ greater than $\tau_{oL}$. Recalibration of the sensing instrument is therefore unnecessary.

DETAILED DESCRIPTION OF THE PREFERRED EMBODIMENTS

Figure 1:
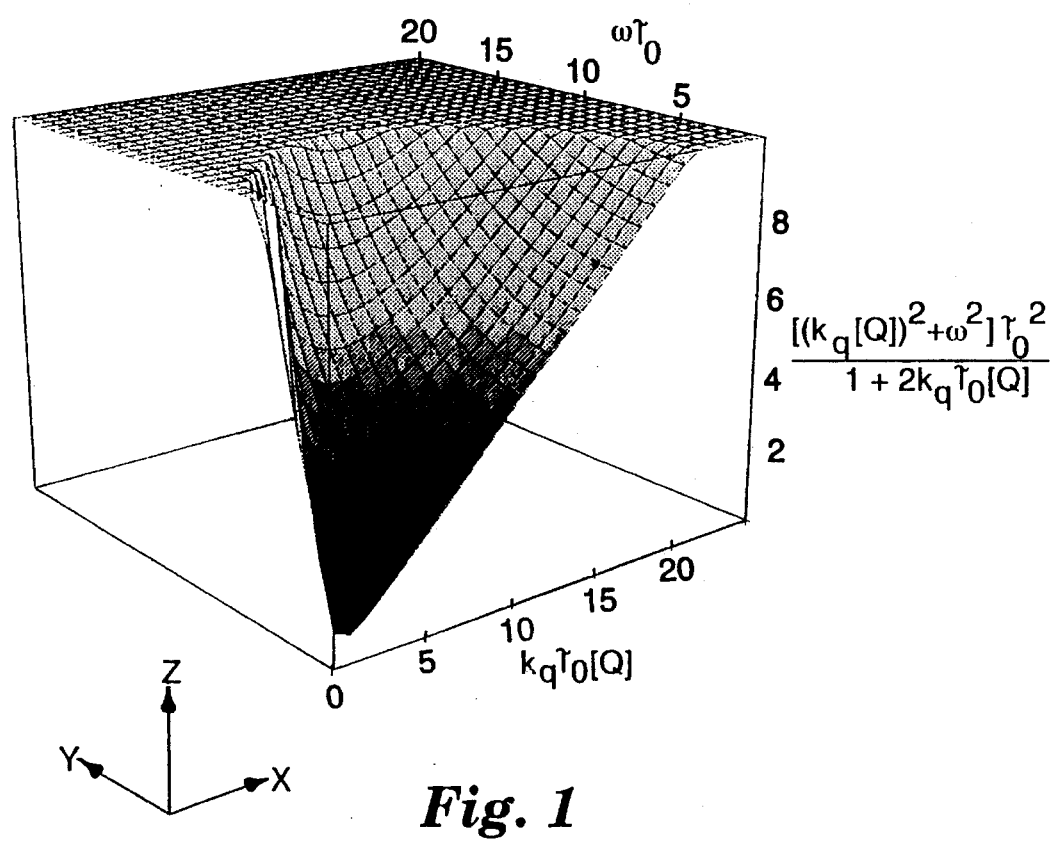
FIG. 1 is a three dimensional illustration of the quantity $[[(k_q[Q])^2+\omega^2]\tau_o^2]/[1+2k_q\tau_o[Q]]$ as a function of the quantities $\omega\tau_o$ and $k_q\tau_o[Q]$.

As used herein, the terms "emissive indicator" or "fluorophore" refer to any species that produces a signal, such as an optically detectable signal, in response to being exposed to an excitation signal, such as an excitation light signal, and wherein said emissive signal (also referred to as the "emitted" signal) is dynamically quenched by an analyte or an analyte-related quencher.

As used herein, the term "monomeric component" refers to a species which may or may not itself provide a signal, such as an optically detectable signal, in response to being exposed to an excitation signal, such as an excitation light signal, and which is capable of participating in the formation of an excited state complex.

As used herein, the term "monomeric indicator component" refers to a monomeric component which provides a signal, preferably an optically detectable signal, in response to being exposed to an excitation signal, preferably an excitation light signal.

As used herein, the term "excimer component" refers to an excited state complex between two monomeric indicator components which have the same indicator structure and which provides a "second emitted signal" wherein said second emitted signal is dynamically quenched by an analyte or an analyte-related quencher. Isomers and tautomers of the same monomeric indicator components are included.

As used herein, the term "exciplex component" refers to an excited state complex between two different monomeric components at least one of which is a monomeric indicator component and which provides a "second emitted signal", wherein said second emitted signal is dynamically quenched by an analyte or an analyte-related quencher.

For brevity, the excimer component and exciplex component will sometimes be generically referred to as the "excited state complex". Also for brevity, the use of a parenthetical "s" will refer to either the singular or plural of the attached word (e.g., "component(s)" refers to either a single component or a plurality of components).

Phase-modulation, fluorescence-based sensors of the present invention are based on the discovery that the slopes of the monitored relationship between the concentration dependent parameter (e.g., phase shift) and the analyte concentration is independent of the excited state lifetime of the fluorophore in the absence of quencher, $\tau_o$, and also independent of heterogeneity and other variations between the intrinsic lifetimes of each emissive state that contributes to the monitored relationship if the condition set forth in Equation 1 below is met for each $\tau_o$.

$$[(k_q[Q])^2+\omega^2]\tau_o^2 >> 1+2k_q\tau_o[Q] \qquad \text{Eq. 1}$$

where:

[Q] is the quencher concentration (e.g., the analyte concentration in the sensing element or matrix);

$k_q$ is the bimolecular quenching rate constant;

$\omega=2\pi f$ is the radial modulation frequency.

In practice, phase-modulation detection can be implemented in a number of different modes, all of which generate a concentration dependent parameter which varies as a function of the analyte concentration when exposed to the excitation signal in the presence of quencher. These phase-modulation detection modes include:

1. Phase shift vs. analyte concentration at constant modulation frequency;

2. Demodulation factor vs. analyte concentration at constant modulation frequency;

3. Modulation frequency vs. analyte concentration at constant phase shift; and

4. Modulation frequency vs. analyte concentration at constant demodulation factor.

The above modes can be characterized as "univariant" systems in that the excitation system is configured to keep one parameter of the excitation signal (e.g., modulation frequency) or emission signal (e.g., phase shift or demodulation factor) constant as the concentration dependent parameter is monitored. In these univariant systems the monitored parameter can be univariantly processed to derive the analyte concentration, without directly or even indirectly making a lifetime determination or calculating the Stern-Volmer slope.

In contrast, sensing instruments such as described in The BOC Group, Inc. European Patent Application Publication Nos. 442 276 A1 and 442 295 A2 are characterized as "multivariant" systems since the excitation signal contains a broad range of frequencies and the phase shift and/or demodulation factor at each of several frequencies is used in determination of analyte concentration. Multivariant systems of this type require deconvolution of the emission signal, e.g., by Fourier analysis software. The frequency domain information derived by this multivariant processing approach is further processed to obtain values for lifetimes or Stern-Volmer slopes, and these values are in turn translated into analyte concentration. A disadvantage of these multivariant sensing instruments is the additional complexity required for the excitation system, detector and processor to serially or simultaneously operate at many frequencies for each analyte.

For sensors operating univariantly under the condition set forth in Equation 1, the analyte dependent decrease in fluorescence intensity, $I_i$, for each $\tau_o$ offsets the analyte dependent increase in modulation factor, $m_i$, for each $\tau_o$ to such an extent that the modulated amplitude for each $\tau_o$ approaches a limit, $m_i I_i = I_{oi}/\omega\tau_{oi}$, where they become independent of analyte concentration. Thus, the relative contribution of the emission signal for each $\tau_o$, to the overall measured phase shift does not change appreciably with analyte concentration or modulation frequency. Assuming the bimolecular quenching constant $k_q$ is the same for each of the quenchable emission signals, the calibration slope for these sensors becomes invariant. The intercept of the relationship between the concentration dependent parameter and the analyte concentration is still susceptible to $\tau_o$ variability, but the slope of this relationship is not. If, in addition to satisfying equation 1, the sensor is configured to satisfy the condition $k_q\tau_o[Q]>9$, then both slope and intercept of the relationship between the concentration dependent parameter and analyte concentration is independent of $\tau_o$ variability for all analyte concentrations within the operating range and for all lifetimes $\tau_o$ greater than $\tau_{oL}$.

Sensing instruments with this operating characteristic have significant advantages. In particular, the slope or slope and intercept of the relationship between the concentration dependent parameter and the analyte concentration will be insensitive to $\tau_o$ heterogeneity or variability due to variable manufacturing process parameters which result in sensor-to-sensor dye mixture variations, and due to photodegradation and dye aggregation which occur over time in any given sensor. Sensors with calibration slopes that are insensitive to lifetime variations can therefore be recalibrated on the basis of one known analyte concentration (i e., "single point calibration") and a predetermined slope by adjusting only the intercept of the calibration relationship between the concentration dependent parameter and the analyte concentration. For example, an in-vivo sensor used to monitor a patient's blood gas (e.g., oxygen) levels can be recalibrated by taking a sample of the blood, measuring the gas concentration of interest by an alternative technique, and simply adjusting the intercept of the measured parameter vs. analyte concentration relationship (i.e., the calibration information) of the sensor so the sensor provides an output reading equal to that measured by the alternative measurement technique. The ability to recalibrate sensors in-vivo enhances the acceptance of sensors of these type by the medical profession. Sensing instruments with calibration slopes and intercepts that are insensitive to lifetime variations never need to be recalibrated once they are set up at the assembly facility.

FIG. 1 is a three dimensional illustration of the quantity $[[(k_q[Q])^2+\omega^2]\tau_o^2]/[1+2k_q\tau_o[Q]]$ as a function of the quantities $\omega\tau_o$ and $k_q\tau_o[Q]$. This plot is truncated along the z axis to illustrate the region where the quantity $[(k_q[Q])^2+\omega^2]\tau_o^2$ exceeds the quantity $[1+2k_q\tau_o[Q]]$ by more than a factor of 10. The x+y axes are truncated solely for illustration purposes and are not intended to limit the present invention to upper bounds for either $\omega\tau_o$ or $k_q\tau_o[Q]$. The quantity $\omega\tau_o$ is directly related to and controlled by the frequency at which the excitation signal is modulated. The quantity $k_q\tau_o[Q]$ is related to the fluorescence quenching efficiency of the sensor and is determined by the sensor dyes and/or host matrix. The bottom of the well in FIG. 1 generally characterizes a set of quantities $\omega\tau_o$ and $k_q\tau_o[Q]$ over which traditional sensors are configured to operate. The planar area at the top of FIG. 1 characterizes a set of quantities $\omega\tau_o$ and $k_q\tau_o[Q]$ which satisfy the condition set forth in Equation 1. From FIG. 1 it is evident that sensing instruments in accordance with the present invention can be configured to operate under the condition set forth in Equation 1 in one or more of the following manners:

1. for $\omega\tau_o>10$, Equation 1 is always satisfied for all $[Q]$;
2. for $10>\omega\tau_o>1$, Equation 1 is satisfied for all $[Q]$ where $[[(k_q[Q])^2+\omega^2]\tau_o^2]/[1+2k_q\tau_o[Q]] >10$; or
3. for $k_q\tau_o[Q]>20$, Equation 1 is always satisfied.

Sensing instruments in accordance with the present invention are configured to monitor analytes having concentrations within a predetermined operating range of concentrations. The sensors are also configured to provide the measurements to an accuracy within a predetermined range of error. Depending upon the range of concentrations over which the sensor must be capable of operating and the degree of accuracy to which the measurements must be made, there can be a set of operating points between the bottom of the well and the planar area in FIG. 1 at which the slopes of the relationship between the concentration dependent parameter and the analyte concentration are sufficiently independent of $\tau_o$ variability to enable the sensor to utilize the discovery of the present invention and provide measurements within the predetermined range of accuracy for all concentrations of interest. In this document, the terms "independent of $\tau_o$ variability" and "sufficiently independent of $\tau_o$ variability" mean independence to such an extent that for all emissive indicator lifetimes which are present in the sensing instrument and have a lifetime greater than a lower lifetime limit $\tau_{oL}$, changes to calibration slopes or calibration slopes and intercepts caused by variations in such lifetimes will not, when combined with other sources of instrument errors, cause the sensing instrument to operate outside of its predetermined range of error. It is understood that some amount of an impurity fluorescence having a lifetime less than $\tau_{oL}$ can be tolerated in instruments of the present invention so long as the contribution of this impurity fluorescence to the detected emission signal does not substantially influence the calibration slope. Many sensing instruments will be capable of providing measurements to within the predetermined range of accuracy for all concentrations within the predetermined operating range if they are configured to operate under the condition that $10\geq [[(k_q[Q])^2+\omega^2]\tau_o^2]/[1+2k_q\tau_o[Q]]>6$. Still other sensors will be capable of providing measurements to within the predetermined range of accuracy for all concentrations within the predetermined range of interest if they are configured to operate under the condition that $6\geq[[(k_q[Q])^2+\omega^2]\tau_o^2]/[1+2k_q\tau_o[Q]]>4$.

Sensing instruments in accordance with the present invention can be configured to operate using any conventional or otherwise known phase-modulation detection technique. In particular, in addition to being configured to operate as externally referenced, single state systems, the inventive concept can be incorporated into multiple state and/or internally referenced sensing instruments of the type described in commonly assigned U.S. patent application Ser. No. 08/137,289, filed on even date herewith, and entitled "Sensors And Method for Sensing" which is herein incorporated by reference. A feature that distinguishes the present invention from traditional instruments is the selection of a sufficiently high modulation frequency $\omega$ (i.e., a "high frequency" instrument) and/or the selection of sensor dyes and/or host matrixes having high diffusivity and/or solubility characteristics (i.e., a "high diffusivity and/or solubility" instrument) so that the instrument is configured to operate sufficiently within the condition set forth in Equation 1 such that calibration slopes or calibration slopes and intercepts are independent of $\tau_o$ variability.

In the so-called "single-state" sensors, fluorescence occurs from a first excited state and follows promptly after excitation of the fluorophore (i.e., emissive indicator). The first excited state of many fluorophores, however, may react with a second component in the sensing element to generate a second excited state species (e.g., an "excited state complex") which is also capable of fluorescing. Under these circumstances, it is possible to observe two emission signals: fluorescence from unreacted first excited states and fluorescence from the reacted second excited state species. Systems of this type are known as "two-state" or "two state" systems. Typical excited state reactions include excimer and exciplex component formation, excited state protonation and deprotonation and energy transfer. In many cases, the excited state process can be described by a simple two state reaction scheme. Each excited state has its own wavelength of fluorescence and its own excited state lifetime. The first emission signal is shorter in wavelength than the second emission signal.

By way of example, copending U.S. application Ser. No. 08/137,289 identified above describes the use of excimer and exciplex forming two state system fluorophores in internally referenced dynamic fluorescence quenching/phase-modulation sensors. The sensing element can include one or more monomeric components located in or covalently bonded to a matrix material wherein at least one monomeric component is a monomeric indicator component. Each of these monomeric indicator components is capable of providing a first emission signal in response to being exposed to the first excitation signal. The second emission signal is provided by an excited state complex (e.g., an excimer component or a exciplex component) produced from excited state reaction of one of the monomeric component(s). Like the first emission signals, the second emission signals are characterized by a lifetime $\tau_o$, and an intensity $I_o$, in the sensing element in the absence of quencher. In the absence of quencher, the lifetime of the excited state complex is significantly longer than the lifetime Of the unreacted monomer excited state. To the extent that this is true, the excited state complex emission is more extensively quenched by the quencher, Q, when it is present. The fluorescence of the second emission signal from the excited state complex is also dynamically quenched by the quencher. The relationships between these excited state complex lifetimes and intensities in the absence and in the presence of quencher enables determination of the Stern-Volmer behavior for the impulse response of the excited state complex. Phase-modulation detection techniques can therefore be used to determine analyte concentrations. Furthermore, calibration slopes become independent of $\tau_o$ variability in the second emitted signal where the conditions of equation 1 are satisfied for each reacted excited state lifetime $\tau_o$.

Phase-modulation detection in single state system sensing instruments involves referencing the concentration dependent parameter to the externally generated excitation signal. Phase-modulation in two-state systems offers the advantage of internal referencing which alleviates signal distortions and other associated problems caused by instrument offsets or bends in the optical fibers through which the signals are propagated. The concentration dependent parameter from the second (e.g., excimer or exciplex) emission signal can be referenced to the concentration dependent parameter from the first (e.g. monomer) emission signal (i.e., differential quenching). Alternatively, the concentration dependent parameter from the second excited state emission signal can be referenced to either the externally applied excitation signal or to both the externally applied excitation signal and the first emission signal. The first and second emission signals can be separated from one another by optical filters and individually detected. All of the phase-modulation techniques described as modes 1–4.above can be implemented in several manners using internal referencing. By way of example, for multiple state fluorophore sensors, phase-modulation detection using mode 1 above can include a processor configured to calculate the analyte concentration as a function of any one of the following phase relationships:

1. $\Theta_{esc} - \Theta_{monomer}$;
2. $\Theta_{esc} - \Theta_{excitation}$;
3. $(\Theta_{esc} - \Theta_{excitation}) - (\Theta_{monomer} - \Theta_{excitation})$; or
4. $\Theta_{esc} + \Theta_{monomer} - \Theta_{excitation}$.

where:

$\Theta_{excitation}$ is the phase of the excitation signal;
$\Theta_{monomer}$ is the phase of the first emission signal; and
$\Theta_{esc}$ is the phase of the second emission signal (where "esc" refers to excited state complex).

Figure 2:
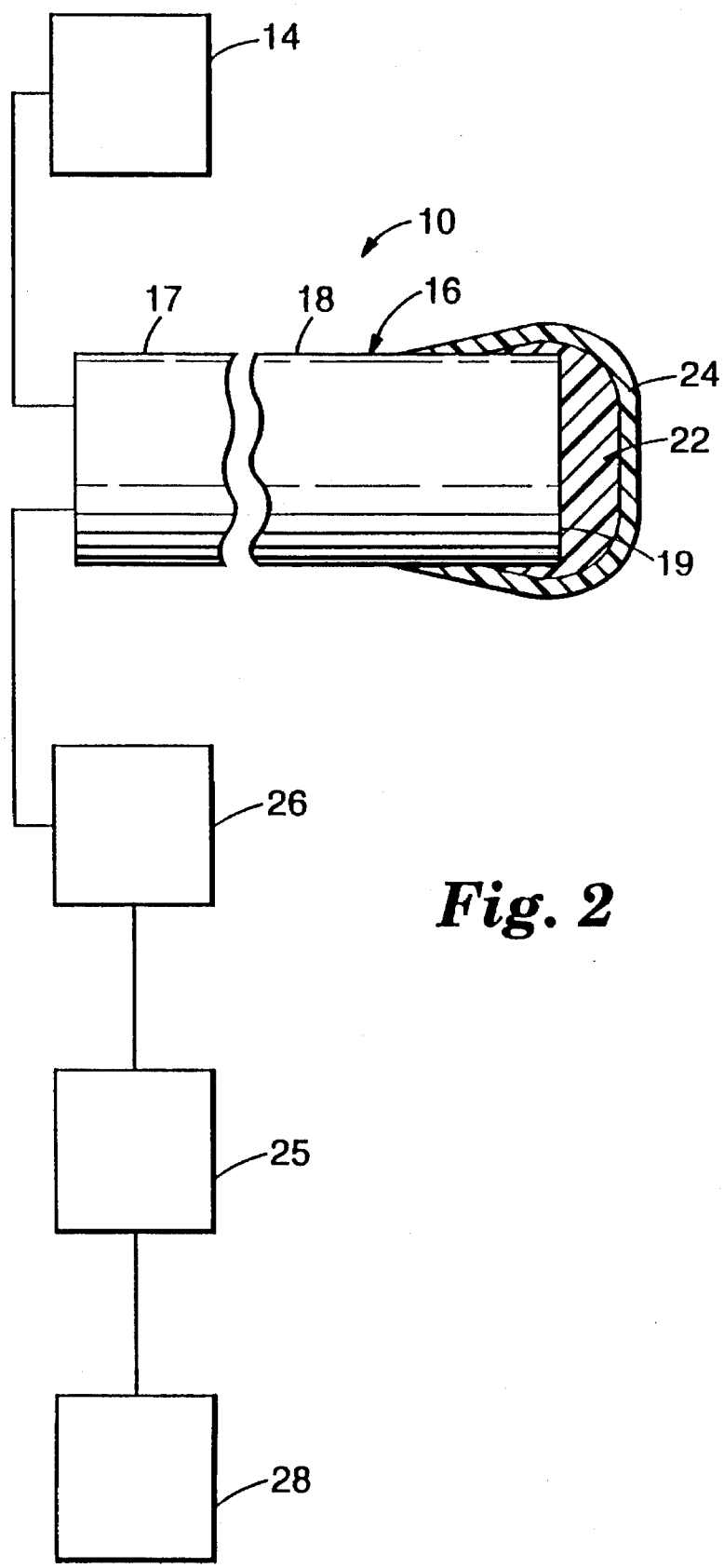
FIG. 2 is a schematic illustration of one embodiment of the sensor apparatus according to the present invention.

A sensing instrument 10 in which the discovery of the present invention can be implemented is illustrated generally in FIG. 2. Instrument 10 includes an excitation system 14 coupled to a sensing probe or element 16. In the embodiment shown, sensing element 16 is coupled to excitation system 14 by one or more optical fibers 17, and includes a section of optical fiber 18 having a distal end or tip with an optical surface 19 coated with a polymer matrix 22. Optical fiber 17 is also coupled to a signal processing system 25 through an optical detector 26. Information representative of measured analyte concentrations can be visually displayed on display 28. Matrix 22 is permeable to the quencher (comprising the analyte of interest or a substance related to the analyte of interest by a known relationship) and includes a dispersion of one or more fluorescable emissive indicators. As illustrated in FIG. 2, the polymer matrix 22 will typically adhere to the sides of the fiber 18 adjacent the optical surface 19, as well as the optical surface itself. An opaque overcoating 24, which can be an iron oxide pigment dispersed in an addition cured polysiloxane, is applied over the totality of the matrix 22 and further down the side of optical fiber 18 than the matrix. Other than being configured with high diffusivity and/or solubility dyes and/or host matrixes which satisfy the relationship set forth in Equation 1 when used in conjunction with the frequency or frequencies at which excitation system 14 is operating, sensing element 16 can be similar to other known or conventional sensing elements.

Other than the requirement that it be capable of operating at high frequency or frequencies which satisfy the relationship set forth in Equation 1 when used in conjunction with the sensor dyes and/or host matrixes of sensing element 16, excitation system 14 can also be similar to other known or conventional excitation systems. Excitation system 14 generates an excitation signal in the form of an intensity modulated light beam. The beam is typically sine wave modulated at one or more radial frequencies, and is coupled to the proximal end of sensing element 16 by optical fiber 17. The excitation signal is propagated to polymer matrix 22 where it excites the fluorescable emissive indicator(s) in the matrix and forces an amplitude modulated optical emission signal. The emission signal will be quenched by the presence of any quencher permeating the matrix, and propagated back through optical fiber 17 to detector 26. Detector 26 converts the optical signals into electrical form for univariant processing by signal processing system 25. Processing system 25, which can be either an analog or digital system, processes the detected signals to derive information representative of analyte concentration. A visual indication of analyte concentration is provided by display 28.

Any one of the phase-modulation detection modes described above can be implemented by sensing instrument 10 to derive the analyte concentration. These phase-modulation modes can be implemented using single state or multiple state indicator components. If multiple state systems are used, the instrument can be configured for either internal or external referencing techniques.

Signal processing system 25 preferably includes memory (not separately shown) for storing calibration information characterizing an expected relationship between a monitored parameter (e.g., phase-shift, frequency or demodulation factor) and analyte concentration. In sensing instruments 10 which include a microprocessor-based or other digital signal processing system 25, the calibration information can be stored as digital information describing an equation functionally relating the monitored parameter to analyte concentration. In such a processing system 25, once the monitored parameter is determined, the equation is solved to obtain the analyte concentration. Alternatively, the processing system 25 can include a stored look-up table of monitored parameter points and associated analyte concentrations. In such a processing system 25, once the monitored parameter is determined, the associated analyte concentration is determined by interpolation from the two closest points stored in the look-up table. Instrumentation processing systems of these types are generally known.

During a single point recalibration, sensing element 16 is exposed to a calibrant having a known analyte concentration, or the concentration of the analyte being monitored is measured using an alternative technique. Using an interface such as a knob or key pad (not shown) coupled to processing system 25, an operator will input information representative of the known analyte concentration. When operated in accordance with the present invention, the processor modifies the stored calibration information in such a manner that the intercept, but not the slope, of the monitored parameter-analyte concentration relationship is varied in such a manner that display 28 provides an output reading equal to the known analyte concentration. Sensing instrument 10 is thereby recalibrated and capable of providing accurate concentration measurements for all concentrations within its operating range. Processing systems capable of modifying the intercept, but not slope, of calibration information in this manner can be implemented using known techniques.

In preferred embodiments, signal processing system 25 univariantly processes the detected excitation signals in real time to derive the monitored parameter. For example, a signal processing system of this type for implementing constant modulation frequency modes 1 and 2 derives phase shift or demodulation factor information, respectively, from the detected emission signals. Stored calibration information characterizing phase shift or demodulation factor as a function of analyte concentration is then accessed as a function of the derived phase shift or demodulation factor, respectively, to obtain the analyte concentration. Indicator component lifetimes are neither directly nor indirectly calculated during this univariant processing technique.

Research and development for the present invention was conducted using a commercially available SLM 48000MHF Fourier Transform Spectrofluorometer instrument manufactured by SLM-Aminco, in conjunction with a 325 nm HeCd laser, as the excitation and signal processing systems. A 364 nm Argon ion laser was also used in certain experiments. This system was configured to provide either a single fixed modulation frequency or a multifrequency burst. Information representative of phase shift and/or demodulation factor (i.e., modes 1 and 2 data) were provided directly by the instrument when it is configured to provide a single modulation frequency. When performing tests with the instrument configured to generate multifrequency bursts, the output data from the instrument is digitized and applied to a computer. This data is then processed using commercially available fast Fourier transform software to determine the phase and demodulation data at each of the multiple modulation frequencies. For two state systems optical filters can be used to separate the different wavelength signals. This instrument can also be operated in a manner which emulates constant phase mode 3. The frequency required to obtain a given phase shift is determined by interpolation.

During experimental procedures, the sensing elements of the type shown at 16 in FIG. 2 were inserted into an enclosure containing gas samples (e.g., mixtures of oxygen and carbon dioxide or nitrogen of known concentrations). In other experimental embodiments of the sensing element (not shown) the fluorescable emissive indicators are dispersed in solutions which effectively function as the matrix. These emissive indicator solutions are held in a thermstatted cuvette. Separate optical fibers (not shown) were used to couple the excitation signal to the sample chamber, and to couple the emission signals from the sample chamber back to the detector.

Figure 3:
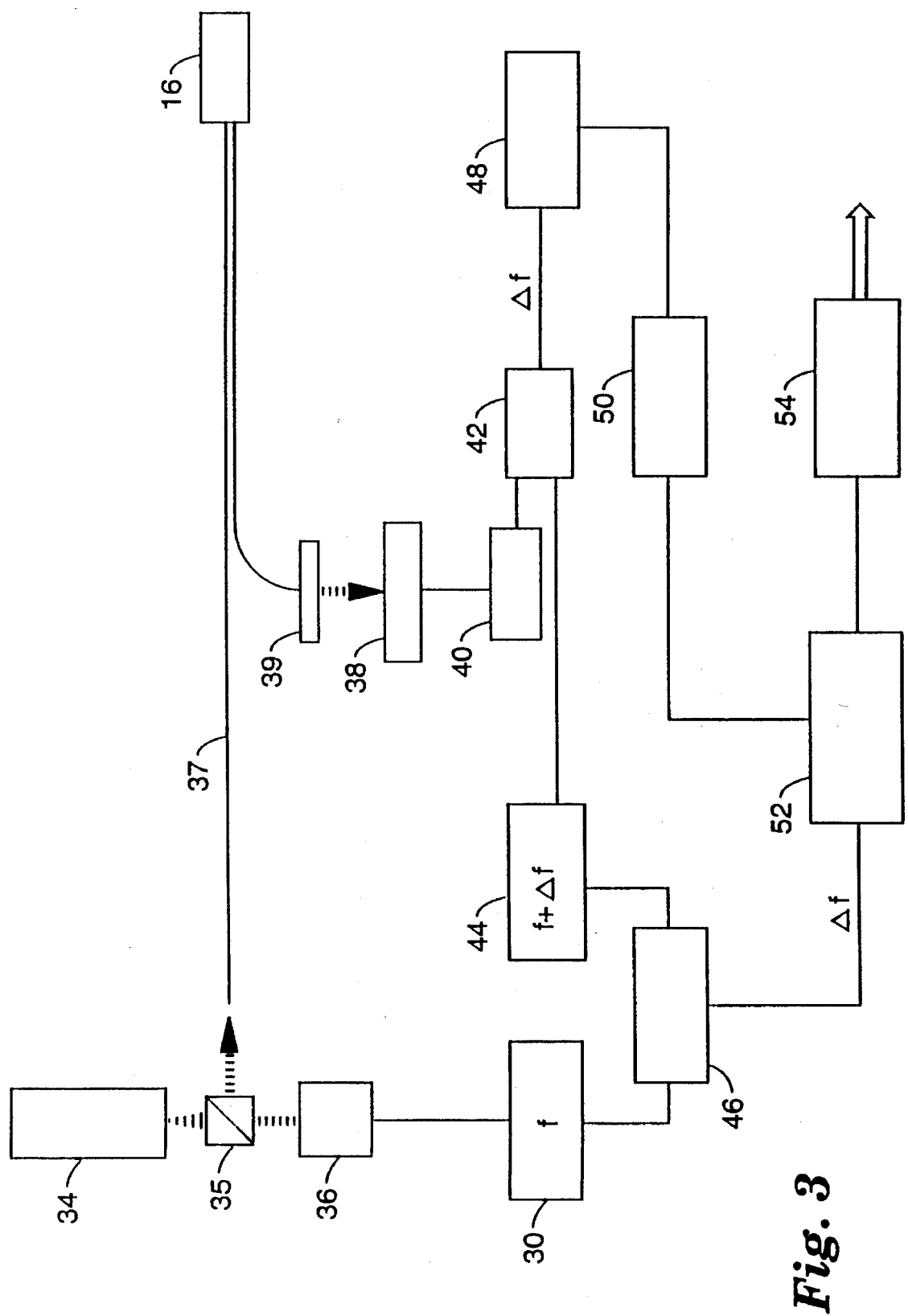
FIG. 3 is a schematic illustration of a sensor system according to the present invention.

Research and development for the present invention has also been conducted using the heterodyne system illustrated in FIG. 3. The system illustrated in FIG. 3 includes an excitation frequency generator 30 for producing a modulation signal at a frequency f. The modulation signal is coupled to an electrooptic modulator 36 (such as a pockels cell) and polarizing beam splitter 35 to modulate an optical excitation signal produced by laser 34. In one embodiment, laser 34 is a 325 nm wavelength HeCd laser. Light emitting diodes or frequency doubled laser diodes can also be used. The modulated excitation signal is directed to sensing element 16 by beam splitter 35 and bifurcated optical fiber 37. The optical emission signal received from sensing element 16 is applied to a detector 38 through an optical filter wheel 39. Filter wheel 39 separates the first and second emission signals provided by sensing element 16 when the sensing element is configured to operate as a two state system, and enables the detection of each emission signal by detector 38 through time division multiplexing. Detector 38 can be a photomultiplier tube, avalanche photodiode or microchannel plate. The detected emission signals are amplified by RF amplifier 40 before being applied to mixer 42.

The embodiment of the system shown in FIG. 3 also includes a frequency generator 44 for generating a signal which differs from the modulation frequency by $\Delta f$. The signal produced by generator 44 and the modulation signal are mixed at mixer 46 to produce a heterodyne reference signal at the frequency $\Delta f$. The signal produced by generator 44 is also mixed with the detected and amplified emission signals at mixer 42 to demodulate the emission signals to the reference frequency $\Delta f$. The demodulated emission signals are amplified by audio amplifier 48 and bandpass filtered by filter 50 to increase the signal to noise ratio and remove unwanted frequency components.

In one embodiment of the system illustrated in FIG. 3, excitation frequency generator 30 produces a 2.00 MHz modulation signal, while frequency generator 44 produces a 2.01 MHz heterodyne signal. The 2.00 MHz detected emission signals outputted by detector 38 are thereby shifted in frequency to 4.01 MHz and 10 KHz at mixer 42. All frequency components other than the 10 KHz signal are filtered out by bandpass filter 50. Similarly, a frequency signal at 10 KHz is provided at the output of mixer 46. The detected emission signals from bandpass filter 50 and the signal from mixer 46 are digitized by digitizer 52 and applied to a signal processor 54. Signal processor 54 is a personal computer in one embodiment, and includes software to derive phase-shifts and demodulation factors for the emission signals relative to the reference signal from mixer 46.

The following non-limiting Examples illustrate certain aspects of the invention. Unless otherwise noted all parts and percentages are by weight and all partial pressures expressed in units of millimeters refer to millimeters of mercury.

EXAMPLES

Example 1

This example illustrates the improved performance of the present invention for the case where two distinct emissive lifetimes characterize the detected emission signal. Using the spectrofluorometer instrument as an excitation and signal processing system and hexane ($ak_q$=6.1×10$^5$ mm$^{-1}$ sec$^{-1}$) as the matrix for the monomeric indicator components, dilute solutions of benzo[g,h,i]perylene (hereinafter "BP"; $\tau_o$= 93 nsec), vinylbenzo[g,h,i] perylene (hereinafter "VBP"; $\tau_o$=35 nsec), and approximately 50:50 mixtures of these two monomeric indicator components were excited in a thermstatted cuvette (maintained at 298 K.) using 364 nm monochromatic excitation provided from an Argon ion laser. Emission was monitored using a 400 nm long pass exit filter. 1,4-Bis(4-methyl-5-phenyloxazol-2-yl)benzene (hereinafter "Me$_2$POPOP"; $\tau_o$= 1.45 nsec) in ethanol was used as an external standard. These solutions were exposed to oxygen in nitrogen mixtures with the following compositions (% oxygen=0.0, 5.22, 10.25, 15.11, and air). Measured phase shifts and demodulation ratios for BP, VBP and a mixture of BP and VBP as a function of O$_2$ partial pressure and modulation frequency are presented in Tables 1a, 1b, 1c, 1d, 1e, and 1f. The measured phase shift data has been rounded to two decimal place accuracy. The measured demodulation ratio has been rounded to three decimal place accuracy.

TABLE 1a

Phase Shift (degrees) - (BP; $\tau_0 = 93$ nsec)

| % $O_2$ | Modulation Frequency (MHz) | | | | | | | | | |
|---|---|---|---|---|---|---|---|---|---|---|
| | 5 | 10 | 15 | 20 | 25 | 30 | 35 | 40 | 45 | 50 |
| 0 | 69.75 | 77.65 | 79.69 | 80.66 | 81.00 | 81.66 | 82.87 | 82.78 | 83.47 | 83.49 |
| 5.22 | 40.19 | 58.09 | 65.99 | 70.01 | 72.64 | 74.54 | 75.89 | 77.09 | 77.85 | 78.35 |
| 10.25 | 29.87 | 48.16 | 58.05 | 63.64 | 67.28 | 69.91 | 72.00 | 73.51 | 75.00 | 75.98 |
| 15.11 | 22.30 | 39.01 | 49.80 | 56.66 | 61.44 | 64.83 | 67.50 | 69.45 | 71.42 | 72.74 |
| 20.95 | 18.00 | 32.56 | 43.07 | 50.54 | 55.91 | 59.99 | 63.06 | 65.53 | 67.64 | 69.44 |

TABLE 1b

Demodulation Factor - (BP; $\tau_0 = 93$ nsec)

| % $O_2$ | Modulation Frequency (MHz) | | | | | | | | | |
|---|---|---|---|---|---|---|---|---|---|---|
| | 5 | 10 | 15 | 20 | 25 | 30 | 35 | 40 | 45 | 50 |
| 0 | 0.325 | 0.170 | 0.118 | 0.090 | 0.073 | 0.063 | 0.054 | 0.048 | 0.043 | 0.039 |
| 5.22 | 0.750 | 0.498 | 0.362 | 0.284 | 0.234 | 0.199 | 0.173 | 0.154 | 0.137 | 0.126 |
| 10.25 | 0.852 | 0.640 | 0.490 | 0.394 | 0.328 | 0.282 | 0.248 | 0.220 | 0.198 | 0.180 |
| 15.11 | 0.918 | 0.761 | 0.620 | 0.513 | 0.436 | 0.377 | 0.334 | 0.299 | 0.269 | 0.246 |
| 20.95 | 0.949 | 0.833 | 0.710 | 0.606 | 0.523 | 0.460 | 0.408 | 0.367 | 0.334 | 0.305 |

TABLE 1c

Phase Shift (degrees) - (VBP; $\tau_0 = 35$ nsec)

| % $O_2$ | Modulation Frequency (MHz) | | | | | | | | | |
|---|---|---|---|---|---|---|---|---|---|---|
| | 5 | 10 | 15 | 20 | 25 | 30 | 35 | 40 | 45 | 50 |
| 0 | 45.19 | 62.99 | 70.62 | 74.50 | 77.29 | 78.98 | 80.37 | 81.03 | 81.84 | 82.21 |
| 5.22 | 28.30 | 46.87 | 57.52 | 63.94 | 68.29 | 71.22 | 73.49 | 75.20 | 76.49 | 77.45 |
| 10.25 | 21.37 | 37.73 | 49.08 | 56.44 | 61.82 | 65.65 | 68.42 | 70.68 | 72.47 | 74.01 |
| 15.11 | 17.21 | 31.47 | 42.42 | 50.32 | 56.12 | 60.55 | 63.84 | 66.63 | 68.69 | 70.58 |
| 20.95 | 13.90 | 26.21 | 36.31 | 44.01 | 50.16 | 54.93 | 58.68 | 61.81 | 64.26 | 66.46 |

TABLE 1d

Demodulation Factor - (VBP; $\tau_0 = 35$ nsec)

| % $O_2$ | Modulation Frequency (MHz) | | | | | | | | | |
|---|---|---|---|---|---|---|---|---|---|---|
| | 5 | 10 | 15 | 20 | 25 | 30 | 35 | 40 | 45 | 50 |
| 0 | 0.667 | 0.421 | 0.299 | 0.231 | 0.188 | 0.158 | 0.135 | 0.119 | 0.107 | 0.096 |
| 5.22 | 0.873 | 0.673 | 0.522 | 0.419 | 0.348 | 0.296 | 0.258 | 0.228 | 0.205 | 0.186 |
| 10.25 | 0.924 | 0.778 | 0.640 | 0.533 | 0.452 | 0.390 | 0.344 | 0.305 | 0.275 | 0.250 |
| 15.11 | 0.953 | 0.847 | 0.730 | 0.626 | 0.542 | 0.474 | 0.421 | 0.377 | 0.341 | 0.311 |
| 20.95 | 0.969 | 0.896 | 0.802 | 0.709 | 0.628 | 0.559 | 0.502 | 0.454 | 0.414 | 0.379 |

TABLE 1e

Phase Shift (degrees) - (mixture of BP and VBP)

| % O₂ | Modulation Frequency (MHz) | | | | | | | | |
|---|---|---|---|---|---|---|---|---|---|
| | 5 | 10 | 15 | 20 | 25 | 30 | 35 | 40 | 45 | 50 |
| 0 | 60.40 | 71.02 | 74.67 | 76.81 | 77.95 | 79.24 | 80.18 | 81.13 | 81.68 | 81.74 |
| 5.22 | 36.64 | 53.68 | 62.25 | 66.86 | 70.25 | 72.21 | 73.85 | 75.05 | 76.64 | 77.63 |
| 10.25 | 26.00 | 42.98 | 53.01 | 59.47 | 63.80 | 67.10 | 69.62 | 71.60 | 72.92 | 73.85 |
| 15.11 | 20.75 | 36.43 | 47.12 | 54.22 | 59.23 | 62.96 | 65.62 | 67.85 | 69.77 | 71.19 |
| 20.95 | 16.16 | 29.93 | 40.04 | 47.54 | 52.87 | 57.40 | 60.67 | 63.34 | 65.68 | 67.61 |

TABLE 1f

Demodulaton Factor - (mixture of BP and VBP)

| % O₂ | Modulation Frequency (MHz) | | | | | | | | |
|---|---|---|---|---|---|---|---|---|---|
| | 5 | 10 | 15 | 20 | 25 | 30 | 35 | 40 | 45 | 50 |
| 0 | 0.371 | 0.214 | 0.152 | 0.117 | 0.095 | 0.082 | 0.070 | 0.062 | 0.055 | 0.050 |
| 5.22 | 0.785 | 0.547 | 0.409 | 0.324 | 0.268 | 0.230 | 0.200 | 0.179 | 0.161 | 0.145 |
| 10.25 | 0.887 | 0.701 | 0.558 | 0.458 | 0.386 | 0.332 | 0.291 | 0.261 | 0.233 | 0.212 |
| 15.11 | 0.927 | 0.783 | 0.650 | 0.545 | 0.466 | 0.406 | 0.359 | 0.322 | 0.291 | 0.265 |
| 20.95 | 0.970 | 0.868 | 0.757 | 0.658 | 0.576 | 0.508 | 0.454 | 0.409 | 0.372 | 0.342 |

Figure 4:
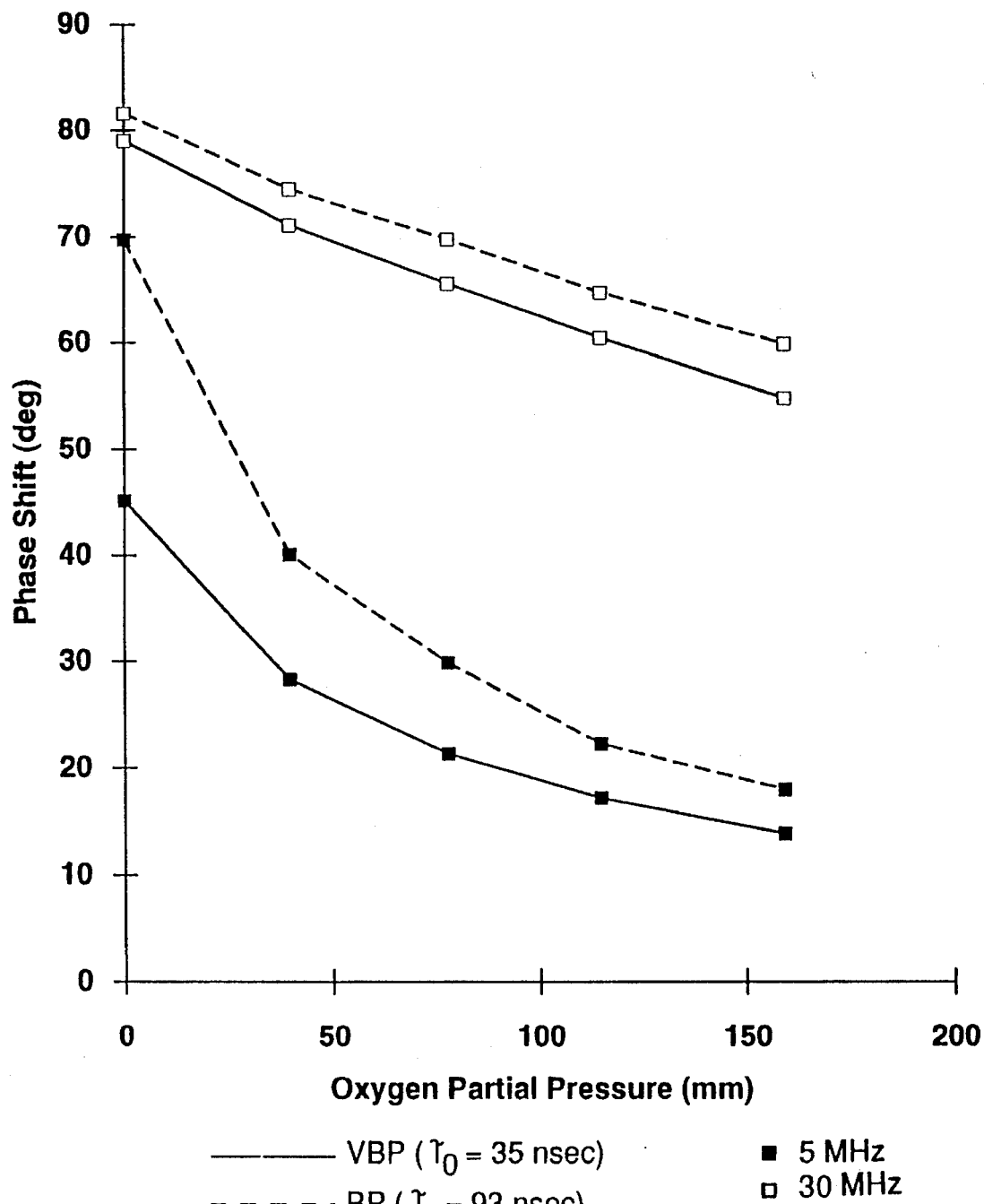
FIGS. 4 and 5 are graphs illustrating the effect of modulation frequency on the measured phase shifts and demodulation ratios for two monomeric indicator components as a function of oxygen partial pressure.
Figure 5:
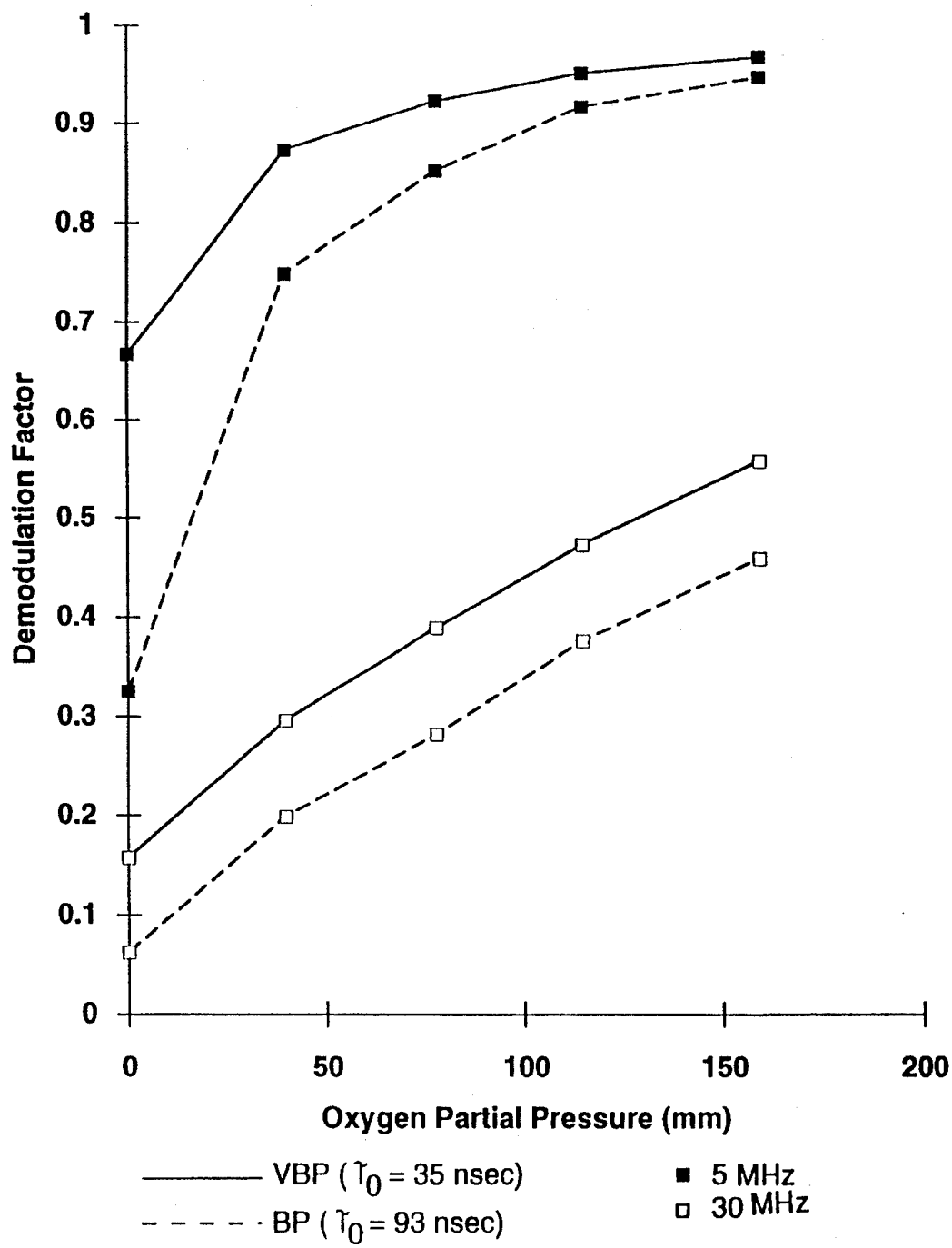
Figure 6:
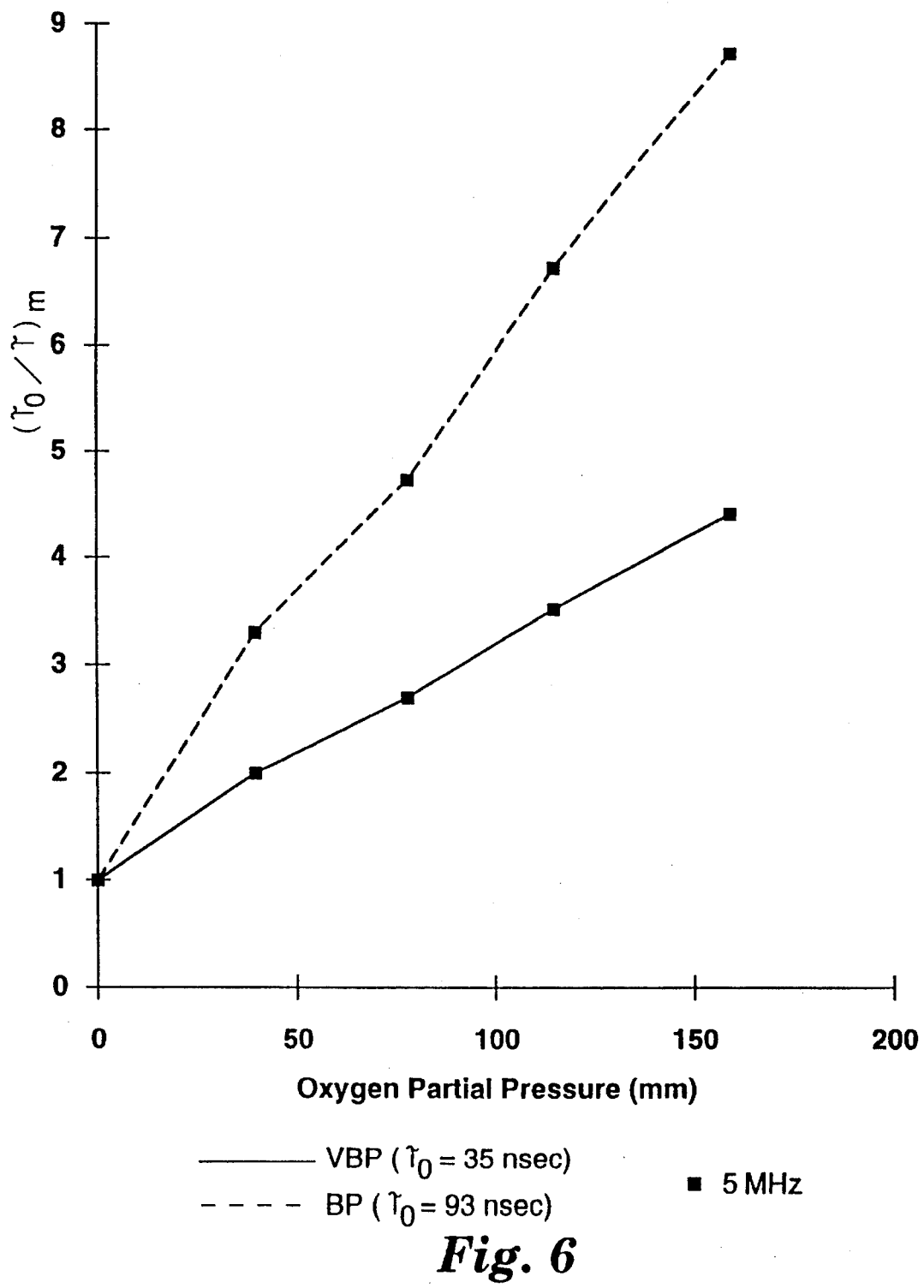
FIG. 6 is a graph illustrating Stern-Volmer plots for the indicators of FIGS. 4 and 5.

Measured phase shifts and demodulation ratios for BP and VBP are presented as a function of $O_2$ partial pressure for 5 and 30 MHz modulation frequencies in FIGS. 4 and 5. The corresponding Stern-Volmer plots for these two solutions were determined from the 5 MHz demodulation factors according to $\tau_o/\tau=[[1/(m_o^2-1)]/[1/(m^2-1)]]^{1/2}$, and are graphically illustrated in FIG. 6. No attempt was made to "fit" the experimental data to a mathematically straight line (such as a "least squares" fit). Instead, for clarity, adjacent experimental points for each solution were individually connected by a straight line segment. For example, in FIG. 6 the resulting connected data points form a somewhat jagged line which is generally straight. The dashed line formed through the solid squares is BP at 5 MHz, and the dashed line formed through open squares is BP at 30 MHz in FIGS. 4–6. Similarly, the solid line formed through the solid squares is VBP at 5 MHz, while the solid line formed through the open squares is VBP at 30 MHz in these Figures.

Note the difference in Stern-Volmer slopes for BP vs. VBP, reflecting the difference in $\tau_o$ for these two dyes. Correspondingly, the 5 MHz phase and demodulation plots for both dyes are curved and are not parallel, consistent with the general expressions $\tan\Theta=\omega\tau$ and $m=(1+\omega^2\tau^2)^{-1/2}$, where $\tau$ is defined by the Stern-Volmer equation, $\tau_o/\tau=1+k_q\tau_o[O_2]$. This 5 MHz frequency data illustrates operation of the instrument in the conventional manner known in the prior art. For VBP, $\omega\tau_o=1.1$, $[[(k_q[Q])^2+\omega^2]\tau_o^2]/[1+2k_q\tau_o[Q]]=0.72$ to 1.27 and $k_q\tau_o[Q]=0.85$ to 2.56 over the clinical range of $O_2$ partial pressure of 40 to 120 mm mercury. For BP, $\omega\tau_o=2.9$, $[[(k_q[Q])^2+\omega^2]\tau_o^2]/[1+2k_q\tau_o[Q]]=2.47$ to 3.75 and $k_q\omega_o[Q]=2.27$ to 6.81.

At 30 MHz the instrument is operating under the relationship set forth in Equation 1. For VBP, $\omega\tau_o=6.6$, $[[(k_q[Q])^2+\omega^2]\tau_o^2]/[1+2k_q\tau_o[Q]]=16.3$ to 8.2 and $k_q\tau_o[Q]=0.85$ to 2.56. For BP, $\omega\tau_o=17.4$, $[[(k_q[Q])^2+\omega^2]\tau_o^2]/[1+2k_q\tau_o[Q]]=56.4$ to 24.2 and $k_q\tau_o[Q]=2.27$ to 6.81. The associated calibration plots are essentially linear and parallel, despite the disparity in $\tau_o$.

The phase shift and demodulation ratios depend on $\tau_o$, $ak_q$, and $[O_2]$ as follows:

$$\Theta=\tan^{-1}(2\pi f\tau)=\tan^{-1}(2\pi f\tau_o/(1+ak_q\tau_o[O_2])); \text{ and}$$

$$m=[1+(2\pi f\tau)^2]^{-1/2}=[1+(2\pi f\tau_o/(1+ak_q\tau_o[O_2]))^2]^{-1/2}.$$

Taking the first derivative of $\Theta$ or m with respect to $P_{O2}$, one obtains the general expressions:

$$d\Theta/dP_{O2}=-\omega\tau_o^2 ak_q/\{1+2ak_q\tau_o P_{O2}+(ak_q\tau_o P_{O2})^2+(\omega\tau_o)^2\}$$

$$dm/dP_{O2}=\omega^2\tau_o^3 ak_q/\{1+2ak_q\tau_o P_{O2}+(ak_q\tau_o P_{O2})^2+(\omega\tau_o)^2\}^{3/2}.$$

When the condition of Equation 1 is satisfied both of these expressions becomes independent of $\tau_o$:

$$d\Theta/dP_{O2}\approx-\omega ak_q/\{(ak_q P_{O2})^2+(\omega)^2\}$$

$$dm/dP_{O2}\approx\omega^2 ak_q/\{(ak_q P_{O2})^2+(\omega)^2\}^{3/2}.$$

If, in addition, $\omega>>ak_q P_{O2}$, then $d\Theta/dP_{O2}\approx-ak_q/\omega$ and $dm/dP_{O2}=ak_q/\omega$. In this case, a linear dependence on $P_{O2}$ is obtained. The parallel plots at 30 MHz indicate that $k_q$ is the same for both dyes. Note that $\omega\tau_o$ is only 6.6 for VBP, causing the VBP plot to deviate from linear parallel behavior at small $O_2$ partial pressures below the physiological range of 40–120 mm (i.e., the range of interest). In the region where plots are linear $\Theta\approx\{\pi/2-1/\omega\tau_o-ak_q P_{O2}/\omega\}$ and $m\approx\{1/\omega\tau_o+ak_q P_{O2}/\omega\}$ and the $\tau_o$ dependence of the intercept is clearly established.

Figure 7:
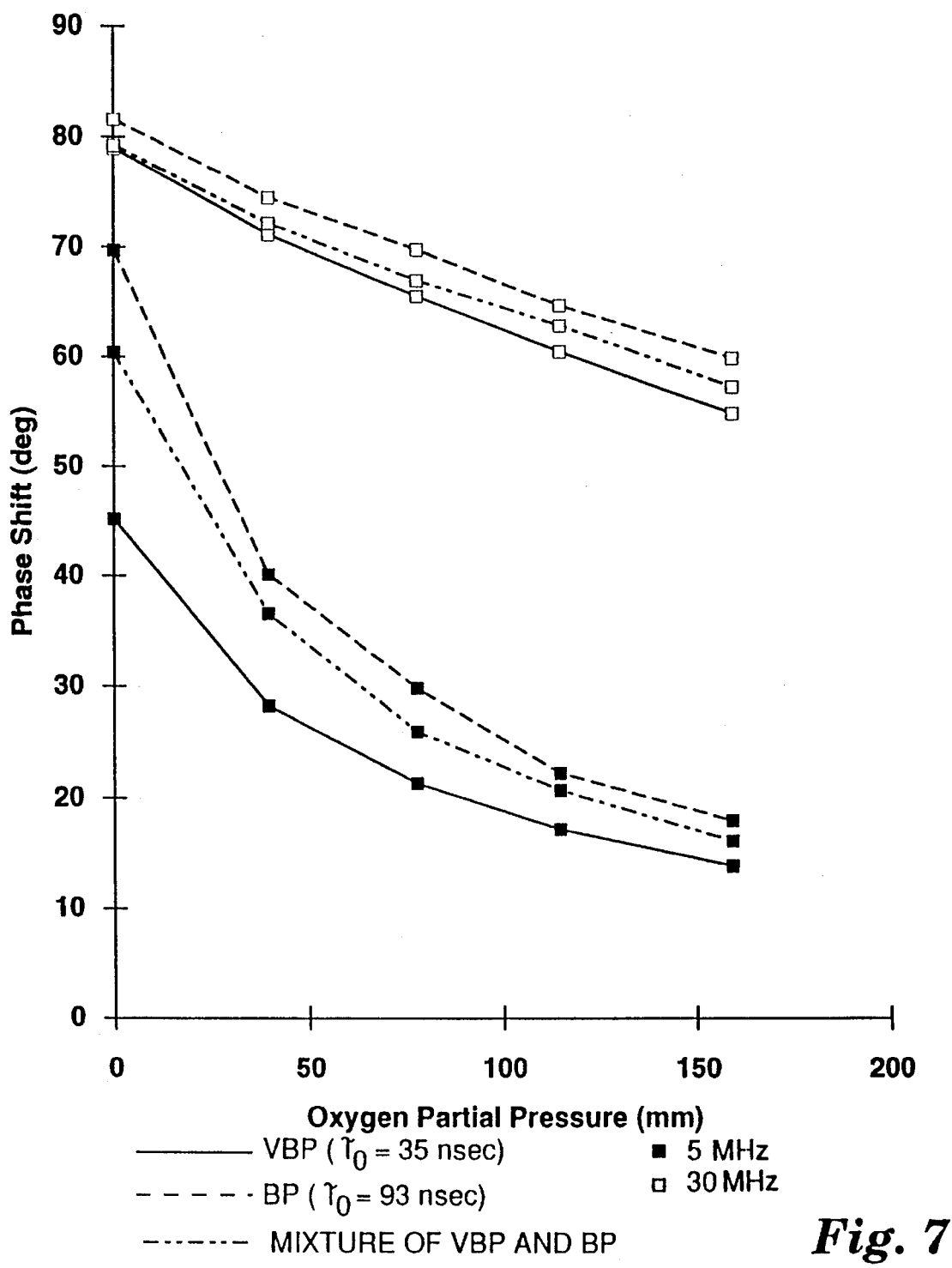
FIGS. 7 and 8 are graphs illustrating calibration data for two monomeric indicator components and a mixture of these two components as a function of modulation frequency.

30 MHz calibration plots for a 50:50 mixture of the two dyes were found to be linear and are shown in FIG. 7, with slopes comparable to those for the pure components and intercepts between those for the pure components. The convention used in FIG. 7 is the same as that in FIGS. 4 to 6. In addition, the intermediate dashed line formed through the solid squares is the mixture at 5 MHz, and the intermediate dashed line formed through the open squares is the mixture at 30 MHz.

If a mixture of the 93 and 35 nsec lifetime indicators exist within the same sensor and specific interactions do not occur, the measured phase shift and demodulation factor can be defined in terms of the phase angles for the individual components as follows:

$$\tan<\Theta>=N/D;$$

$$m=[N^2+D^2]^{1/2};$$

$N = \Sigma f_i \sin \Theta_i \cos \Theta_i;$ $D = \Sigma f_i \cos^2 \Theta_i;$ and $f_i = (\alpha_i I_i / I_{oi}) / (\Sigma \alpha_i I_{oi});$ where: $\Theta_i$ is the phase shift for the individual fluorophore component; $f_i$ is the oxygen dependent contribution of each fluorophore to the total measured fluorescence; and $\alpha_i$ is the contribution of each fluorophore to the total measured fluorescence in the absence of quencher Q.

At the lower operating frequency of 5 MHz, the mixture yielded calibration slopes which deviated substantially from those for the pure components, while at the higher operating frequency of 30 MHz the slope deviation is much less pronounced. To maintain ± 3 mm accuracy, and assuming single point recalibration at 100 mm, a slope precision of about 5% is necessary.

Figure 8:
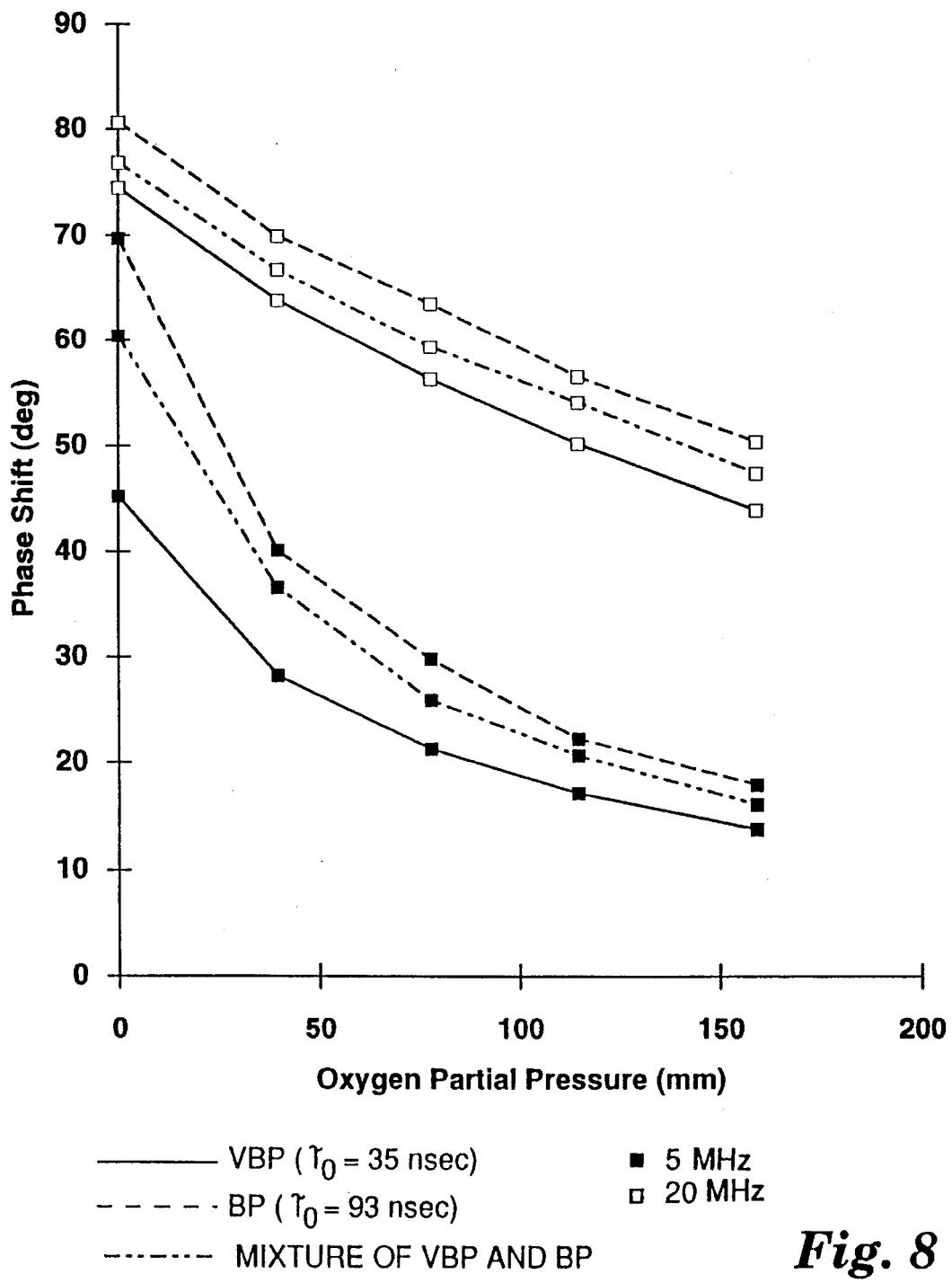

Measured phase shifts for dilute hexane solutions of BP, VPB and a 50:50 mixture of BP and VBP at operating frequencies of 5 and 20 MHz are illustrated in FIG. 8. The lines formed through the solid squares illustrate the 5 MHz data. The lines formed through the open squares illustrate the 20 MHz data. At 20 MHz the instrument is essentially operating within the conditions set forth in Equation 1. For VBP at 20 MHz, $\omega\tau_o = 4.4$, $[[(k_q[Q])^2 + \omega^2]\tau_o^2]/[1 + 2k_q\tau_o[Q]] = 7.4$ to 4.2 and $k_q\tau_o[Q] = 0.85$ to 2.56. For BP at 20 MHz, $\omega\tau_o = 11.7$, $[[(k_q[Q])^2 + \omega^2]\tau_o^2]/[1 + 2k_q\tau_o[Q]] = 25.6$ to 12.5 and $k_q\tau_o[Q] = 2.27$ to 6.81. Although not linear, all the plots have similar slopes.

Example 2

Figure 9:
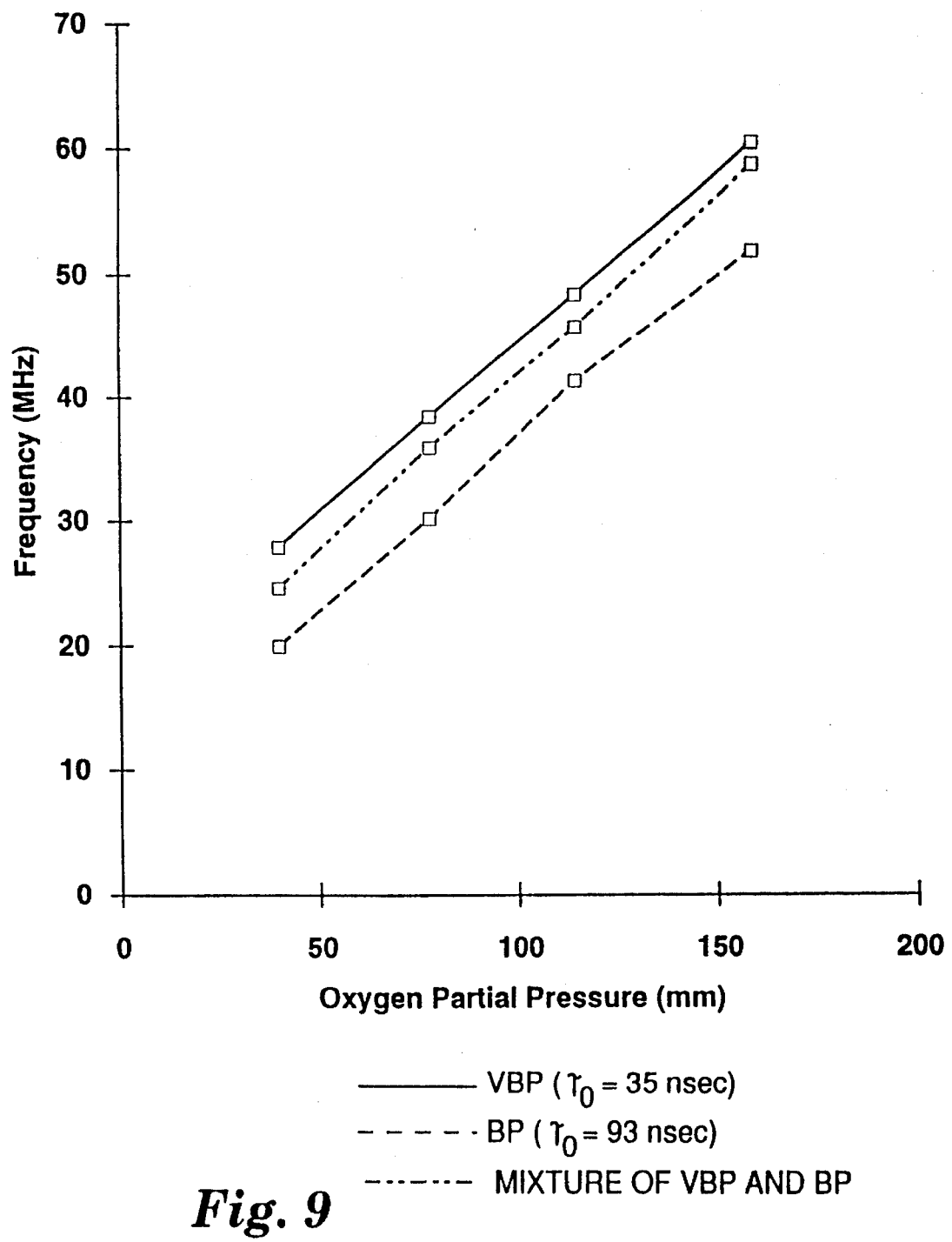
FIG. 9 is a graph of frequency vs. oxygen partial pressure for two monomeric indicator components and a mixture of these two components. (phase-modulation mode 3).

Using the instrumentation and VBP and BP indicator solutions described above in Example 1, and exposed to oxygen in nitrogen mixtures as described in Example 1, phase shifts were determined as a function of $O_2$ partial pressure at several modulation frequencies ranging from 5 to 125 MHz using Multiharmonic Fourier (MHF) Parallel acquisition. By interpolation, modulation frequencies were determined which will give a constant phase shift of 70° at each oxygen concentration. FIG. 9 is a graph of frequency vs. oxygen concentration (i.e., phase-modulation mode 3), and exhibits linear behavior and a constant slope for both the pure components and for the mixture.

Example 3

The sensing element used in this example includes a dimethylsiloxane film containing $2 \times 10^{-5}$ M 1,3-bis (1-pyrenyl) propane, an intramolecular excimer forming molecule. The film was prepared as follows: To 0.50 g of a vinyl terminated siloxane (sold by Petrarch Systems under the trademark PS441) were added 0.05 g of a polymethylhydrosiloxane (available from Petrarch Systems under the trademark PS123), 0.50 ml of a $9 \times 10^{-5}$ M $CH_2Cl_2$ solution of 1,3-bis-(1-pyrene) propane (available from Molecular Probes), and 10 microliters of Pt catalyst solution. The samples were dried in air, and then in a vacuum. The Pt catalyst solution used in these preparations was a solution of Karsted's catalyst in hexane.

Experiments with this sensing element in phase-modulation mode 1 were conducted using the SLM 48000 Frequency-Domain Fluorometer with single frequency acquisition. The sensing film was placed in a thermostatted optical isolation chamber equipped with a port for collinear excitation and emission optical fibers and ports for rapid gas exchange. The fiber optic port was positioned to allow the distal fiber termini to provide for excitation and emission collection at an angle of 45 degrees from the film surface to minimize scatter. The film was excited at 325 nm using monochromatic excitation provided from a HeCd laser. Emission wavelengths of 500 nm for the excimer emission and 375 nm for the monomer emission were serially selected using a standard monochromator. The sensor film was exposed to oxygen in nitrogen mixtures with the following compositions (volume % oxygen=0.0, 5.09, 10.35, 15.37).

Phase shifts for both the monomer and the excimer emissions were obtained from single frequency measurements at 1, 3, 5, 10, 20, 30 and 50 MHz and referenced to the phase shift for $Me_2POPOP$ as an external standard. The phase difference between the monomer and the excimer emissions is given as a function of % $O_2$ and the modulation frequency in Table 3a.

TABLE 3a

| | $\Delta\Theta = \Theta_{excimer} - \Theta_{monomer}$ for $O_2$ Sensor | | | | | | |
|---|---|---|---|---|---|---|---|
| | Modulation Frequency (MHz) | | | | | | |
| % $O_2$ | 1 | 3 | 5 | 10 | 20 | 30 | 50 |
| 0.0 | 19.1 | 46.0 | 59.9 | 74.0 | 81.8 | 84.5 | 86.7 |
| 5.09 | 14.8 | 38.4 | 52.8 | 69.3 | 79.3 | 82.8 | 85.7 |
| 10.37 | 11.7 | 31.9 | 46.0 | 64.3 | 76.4 | 80.9 | 84.5 |
| 15.37 | 10.0 | 27.8 | 41.3 | 60.7 | 74.1 | 79.3 | 83.5 |

Using the phase shift difference at 0.0% $O_2$ and the relationship $\tan(\Delta\Theta) = \omega\tau$, $\tau_o$ characterizing the impulse response function of the excimer was calculated to be about 55 nsec, independent of the modulation frequency (see Table 3b below).

TABLE 3b

| Modulation frequency (MHz) | $\tau_o$ | $K_{sv}$* | $ak_q$** |
|---|---|---|---|
| 1 | 55.1 | 8.31 | 1.51 |
| 3 | 54.9 | 8.27 | 1.51 |
| 5 | 54.9 | 8.28 | 1.51 |
| 10 | 55.5 | 8.31 | 1.50 |
| 20 | 55.2 | 8.41 | 1.52 |
| 30 | 55.1 | 8.27 | 1.50 |
| 50 | 55.2 | 8.36 | 1.51 |

*"$K_{sv}$" = slope of $\tan(\Delta\Theta)_o/\tan(\Delta\Theta)$ vs partial pressure of oxygen in mm. Slope reported in units of $mm^{-1} \times 10^3$.
**"$ak_q$" is determined from $K_{sv}/\tau_o$ and reported in units of $mm^{-1} sec^{-1} \times 10^{-5}$.

Figure 10:
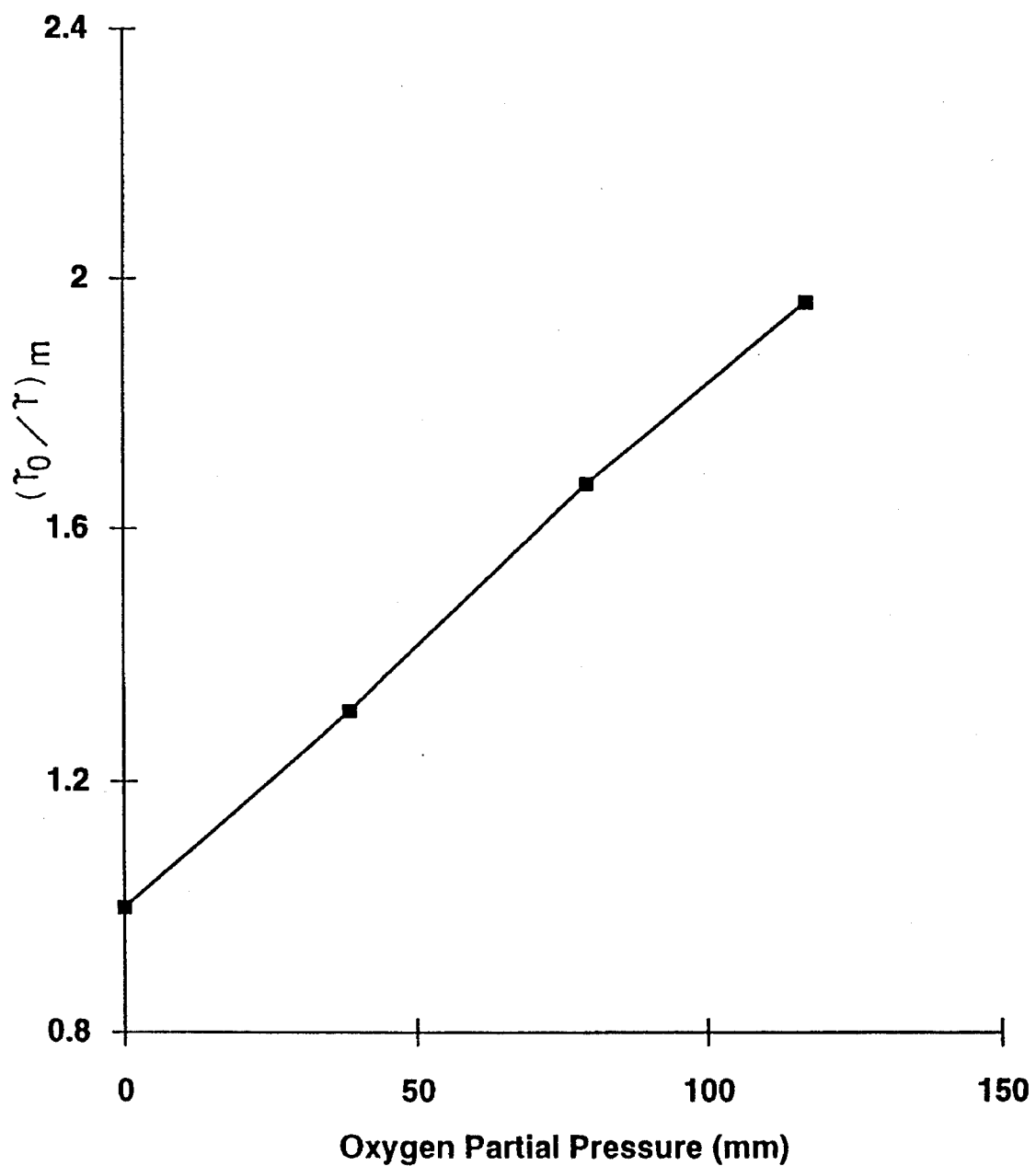
FIG. 10 is a graph illustrating a Stern-Volmer plot for an excimer forming system.

These attributes of the excimer forming system give rise to clean Stern-Volmer quenching behavior for the excimer based on the phase shift difference. This is shown in FIG. 10 for data collected at a modulation frequency of 1 MHz. The Stern-Volmer relationship is $\tau_o/\tau = 1 + ak_q\tau_oP_{O2} = \tan(\Delta\Theta)_o/\tan(\Delta\Theta)$, where $k_q$ is the bimolecular quenching rate constant, a is the solubility of oxygen in the silicone, and $P_{O2}$ is the partial pressure of oxygen in the medium being sensed. The Stern-Volmer slope, $K_{SV} = ak_q\tau_o$, was determined experimentally for each modulation frequency (Table 3b). From values for $K_{SV}$ and $\tau_o$, the quantity $ak_q$ was determined to be approximately $1.51 \times 10^5$ $mm^{-1}$ $sec^{-1}$. This quantity is used below to evaluate the behavior of $\Delta\Theta$ vs $O_2$ calibration plots at high modulation frequency.

Figure 11:
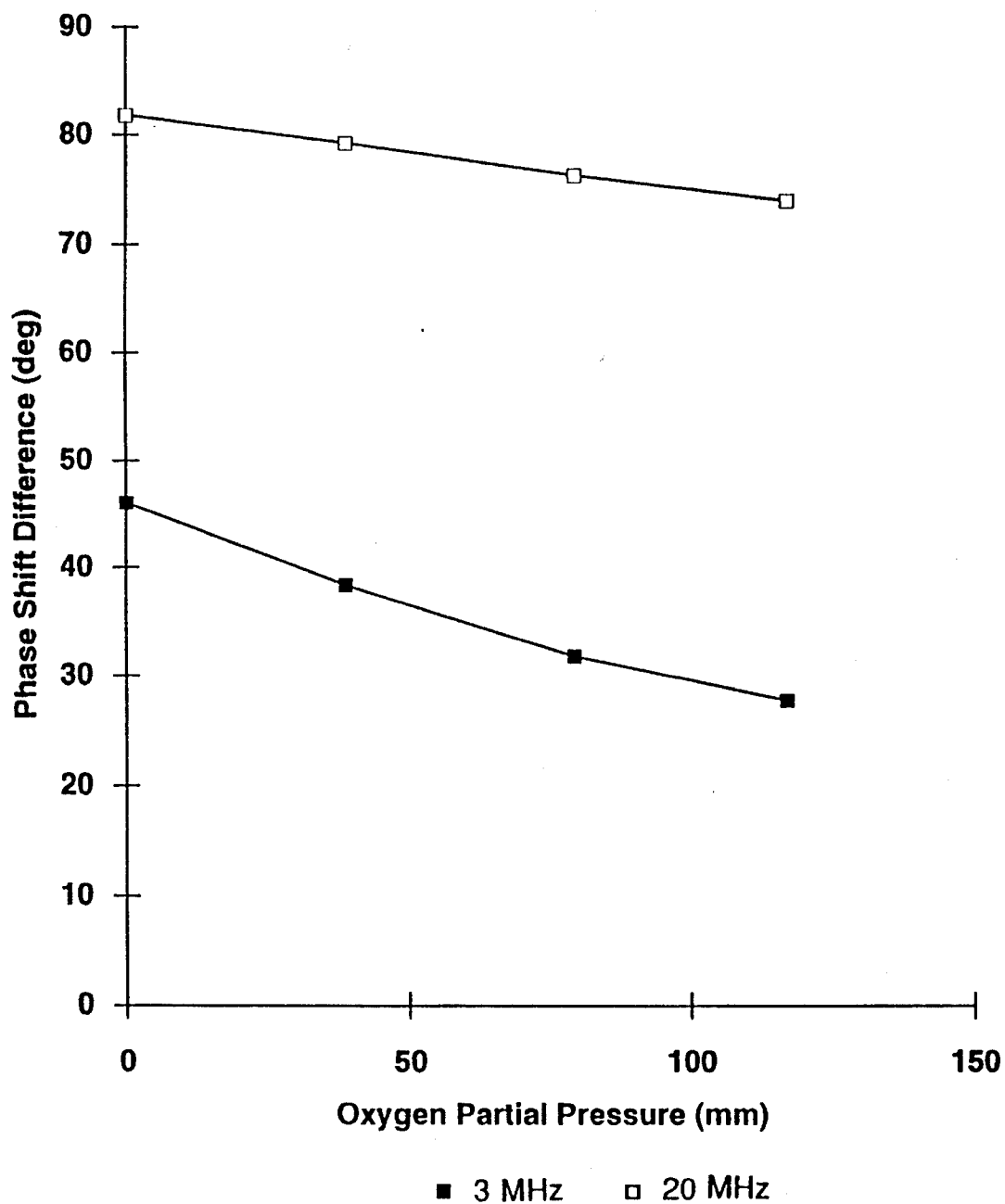
FIG. 11 is a graph illustrating phase shift difference as a function of oxygen partial pressure and at two modulation frequencies for an excimer forming system.

The phase shift difference, $\Delta\Theta$, is presented as a function of $O_2$ partial pressure for modulation frequencies of 3 and 20 MHz in FIG. 11. The 3 MHz phase plot, formed through the solid squares, is curved, consistent with the general expression $\tan\Delta\Theta = \omega\tau = \omega\tau_o/(1 + k_q\tau_oaP_{O2})$. Variation in $\tau_o$ will lead to a family of curves that are not parallel. This 3 MHz frequency illustrates operation of the sensor outside the conditions of equation 1. For this indicator component at 3 MHz and $P_{O_2}$=40 to 120 mm: $\omega\tau_o$=1.04; $[[(k_q[Q])^2+\omega^2]\tau_o^2/[1+2\,k_q\tau_o[Q]]$=0.71 to 0.69; and $k_q\tau_o[Q]$=0.33 to 1.00.

At 20 MHz, the corresponding plot, formed through the open squares, is linear. $\omega\tau_o$=6.91; $[[(k_q[Q])^2+\omega^2]\tau_o^2]/[1+2k_q\tau_o[Q]]$=28.8 to 16.3; and $k_q\tau_o[Q]$=0.33 to 1.00 at this frequency. As in example 1, $\Delta\Theta\approx\{(\pi/2)-(1/\omega\tau_o)-(ak_q P_{O_2}/\omega)\}$. Thus the slope is independent of variations in $\tau_o$, unlike the Stern-Volmer slopes. Using $ak_q$=1.51×10$^5$ mm$^{-1}$sec$^{-1}$ from above, a theoretical slope $ak_q/\omega$=−0.0688 deg/mm is calculated which agrees quite well with the experimental slope of −0.0686 deg/mm, thus confirming the form of the equation in the high frequency limit. Comparison of the calibration slopes at 20, 30 and 50 MHz confirms an inverse dependance of slope on modulation frequency.

Example 4

Figure 12:
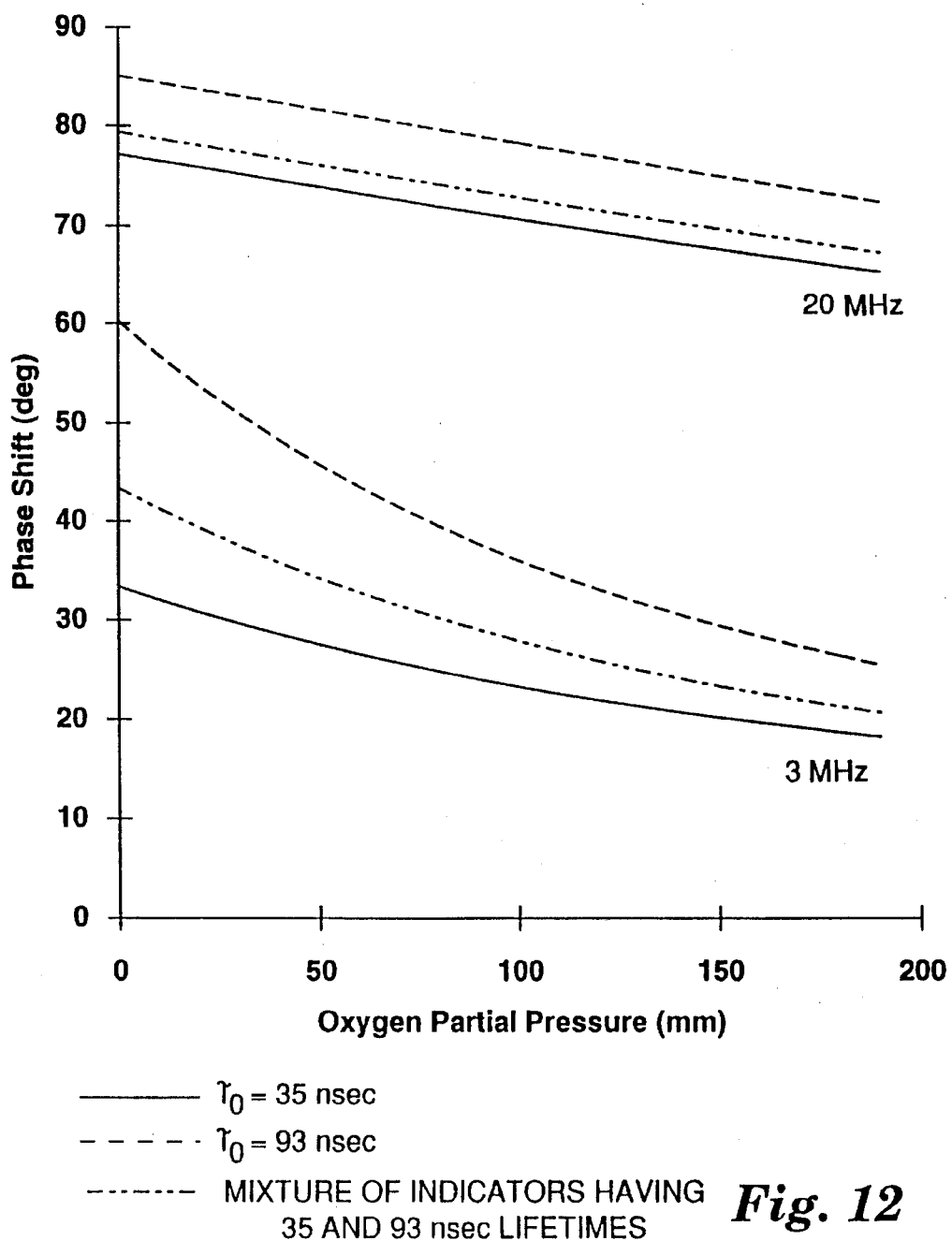
FIGS. 12 and 13 are graphs illustrating calculated calibration data for two monomeric indicator components and a mixture of these components in a silicone rubber matrix as a function of modulation frequency.
Figure 13:
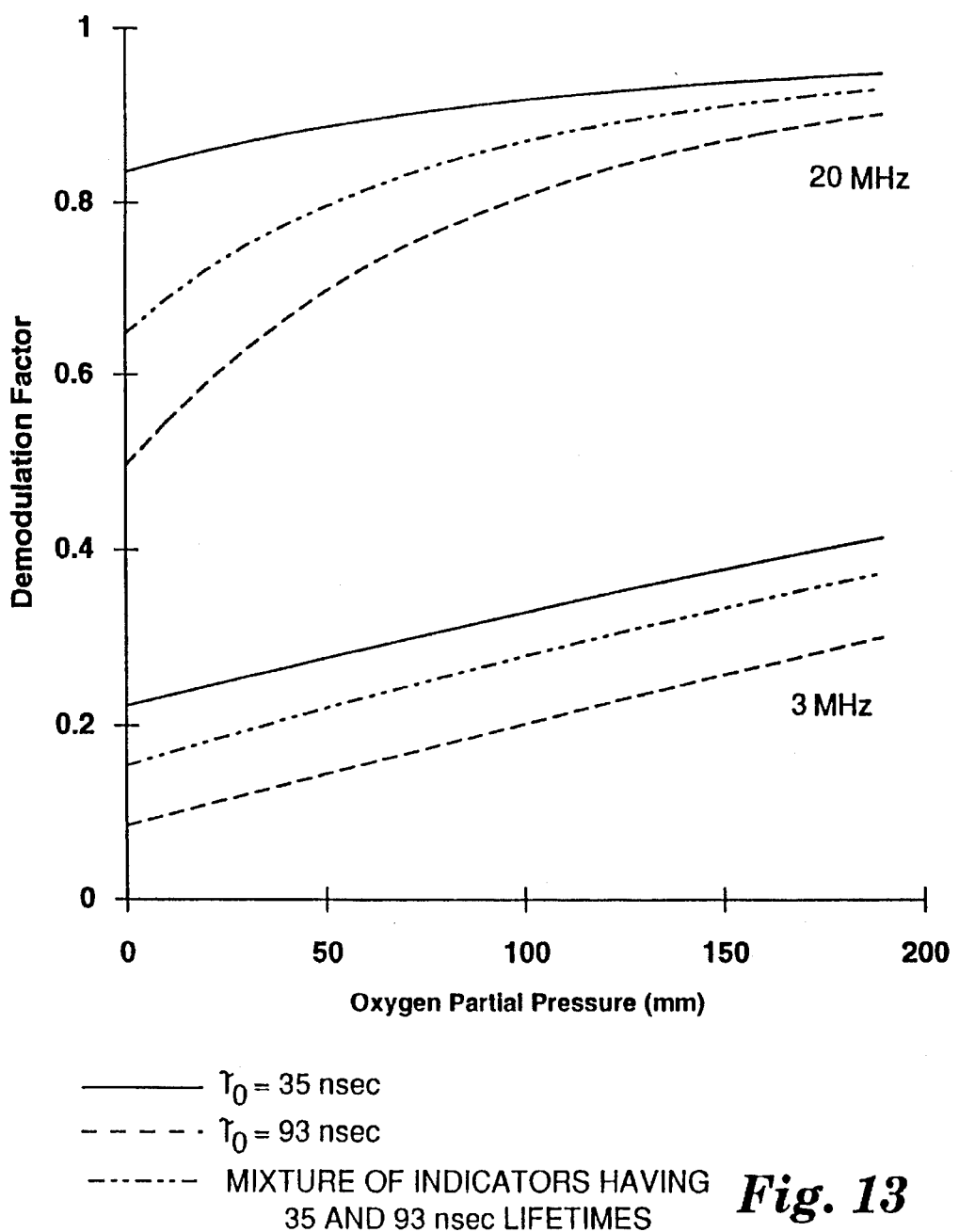

FIG. 12 is a graphic illustration of several sets of calibration data for benzo [g, h, i] perylene (BP; $\tau_o$=93 nsec) and vinylbenzo [g, h, i] perylene (VBP; $\tau_o$=35 nsec) monomeric indicator components, and a 50:50 mixture of these monomeric indicator components in a silicone rubber matrix. These simulations are based on experimentally derived values for $\tau_o$ (from example 1) and $ak_q$ (from example 3=1.5×10$^5$ mm$^{-1}$ sec$^{-1}$). With an excitation signal modulated at 3 MHz, $\omega\tau_o\approx0.66$ for the 35 nsec indicator component and $\omega\tau_o\approx1.76$ for the 93 nsec indicator component. Each set of data characterizes a calibration relationship between measured phase shift $\Theta$ and oxygen concentration (partial pressure). FIG. 13 is a graphic representation of sets of simulated calibration data for the same sensors in phase-modulation mode 2 (demodulation factor m as a function of oxygen concentration). When conventional modulation frequencies are used (i.e., where $\omega\tau\approx1$) calibration data plots of the phase shift and demodulation factor as a function of partial pressure of oxygen for these three sensors exhibit poor behavior (e.g., variable slopes and intercepts) as shown in FIGS. 12 and 13, respectively. In these cases, the modulation frequency is chosen to be 3 MHz, to provide maximum phase accuracy at the midpoint of physiologically relevant partial pressures of oxygen (90 mm $O_2$), for the sensor with $\tau_o$=93 nsec. However, at higher modulation frequencies (20 MHz data shown in FIGS. 12 and 13) the slopes of these calibration plots become independent of $\tau_o$ variability and $\tau_o$ heterogeneity.

Example 5

Figure 14:
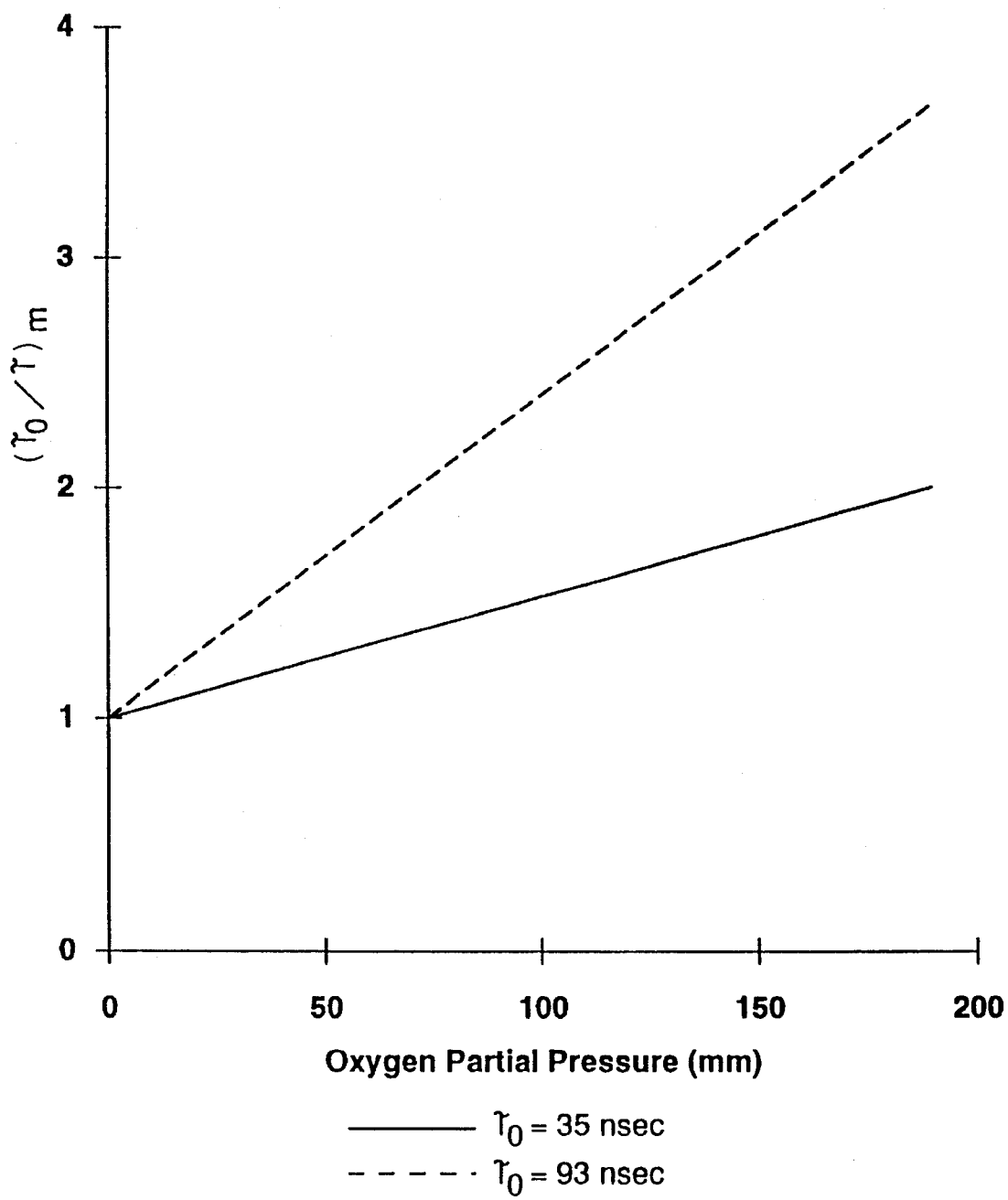
FIG. 14 is a graph illustrating calculated Stern-Volmer plots for the two monomeric indicator components of FIGS. 12 and 13.
Figure 15:
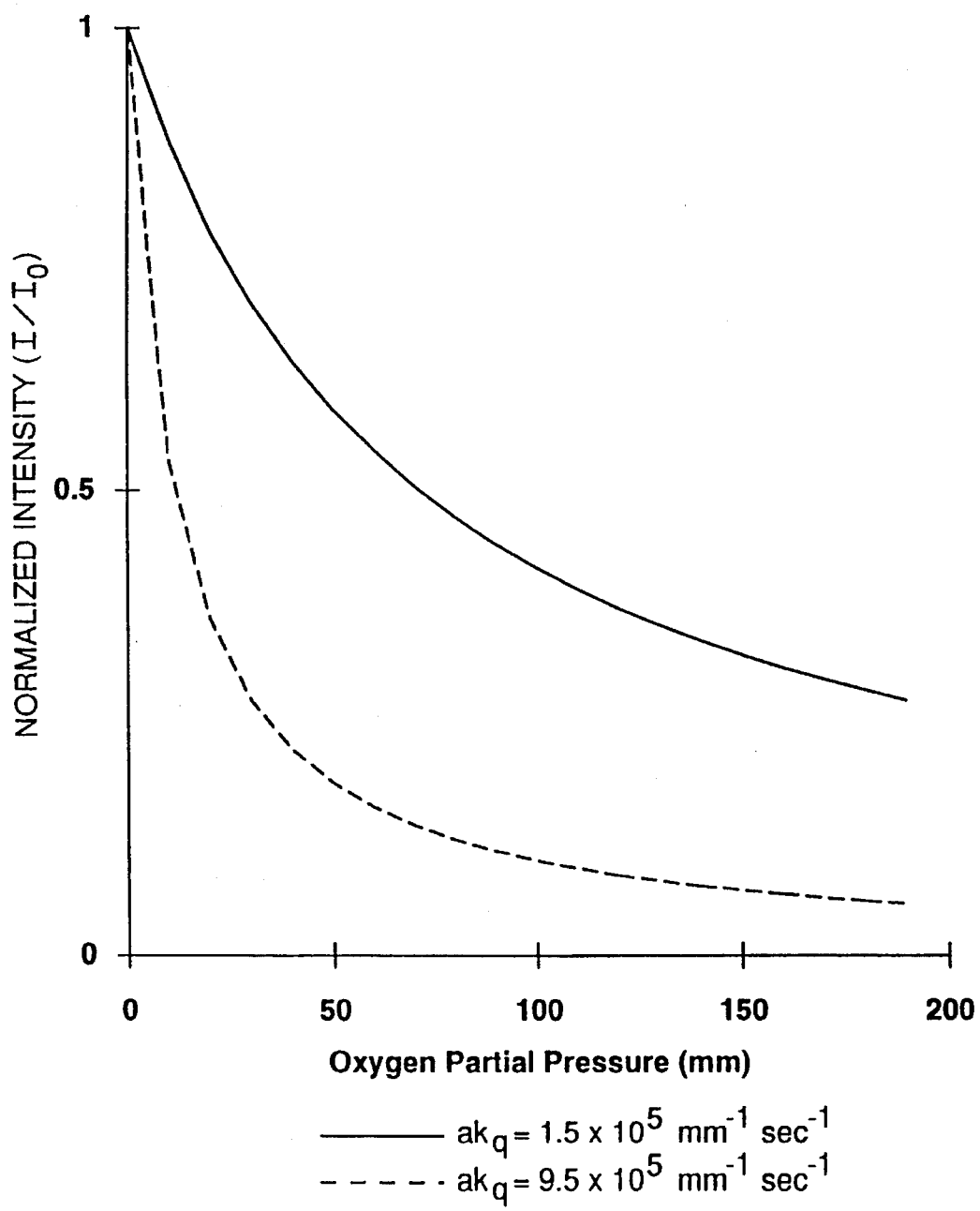
FIG. 15 is a graph illustrating the effect of varying $ak_q$ on the oxygen responsivity of the fluorescence intensity.

The Wolfbeis book discusses in some detail a common oxygen sensor configuration in which a polycyclic aromatic hydrocarbon (PAH) is dispersed in, or covalently attached to, a silicone rubber. In this material, the product of the oxygen solubility term, a, and the diffusion controlled bimolecular quenching rate constant, $k_q$, is approximately 1.5× 10$^5$ mm$^{-1}$ sec$^{-1}$. Excited state lifetimes for typical PAH fluorophores in such a sensing element typically vary from $\tau_o$=20 to 100 nsec, giving rise to Stern-Volmer calibration slopes of $K=ak_q\tau_o$=0.003 to 0.015 mm$^{-1}$. FIG. 14 illustrates a Stern-Volmer plot of fluorescence lifetime vs. partial pressures of oxygen for the oxygen sensing elements described immediately above, where $\tau_o$=35 or 93 nsec. In this case, the solubility and diffusivity of oxygen in the polymer matrix is such that the sensor gives good response sensitivity over the analyte concentration range of interest. For longer lifetime dyes or for polymer matrix hosts where oxygen solubility and diffusivity are much greater, the Stern-Volmer quenching constant can become excessively high. For example, FIG. 15 illustrates the effect of increasing $ak_q$ by a factor of 6.3 from 1.5×10$^5$ mm$^{-1}$ sec$^{-1}$ to 9.5×10$^5$ mm$^{-1}$ sec$^{-1}$ (e.g., by dispersing the PAH indicator components in a different matrix). Specifically, FIG. 15 illustrates this effect for $\tau_o$=93 nsec. If the Stern-Volmer quenching constant becomes excessively high, amplitude sensitivity is reduced over the clinical range of 40 to 120 mm mercury. To overcome this reduced sensitivity according to conventional practice, i.e., as taught by Mauze, one could modify the fluorophore or the matrix polymer properties to decrease $\tau_o$, a, or $k_q$. The Stern-Volmer quenching constant, K, may be decreased through modification of the chemical composition of the sensing element in order to achieve a more desired sensitivity within the analyte concentration range of interest.

Figure 16:
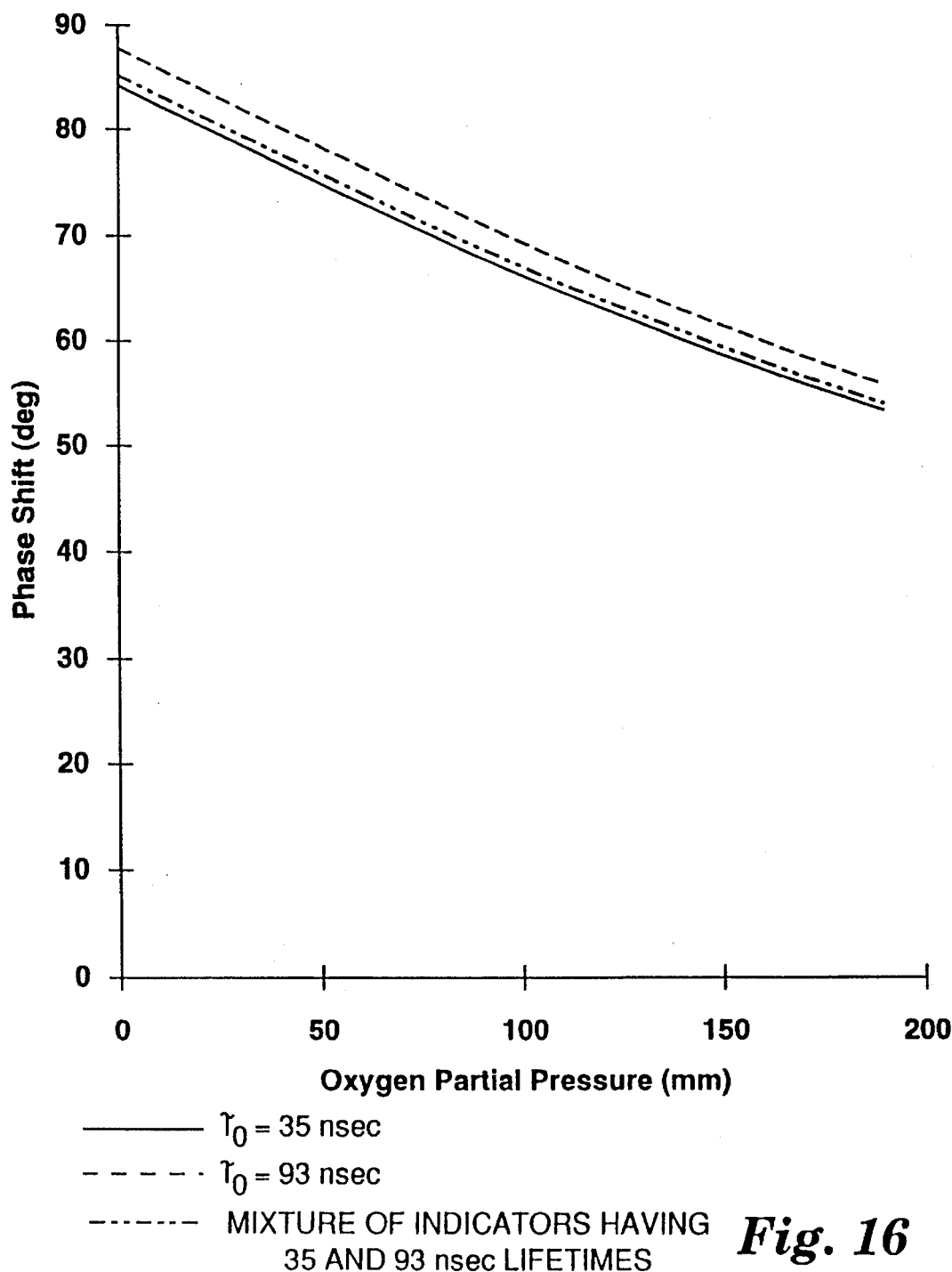
FIGS. 16 and 17 are graphs illustrating calculated calibration data of phase shift and demodulation factor (respectively) vs. oxygen partial pressure for two monomeric indicator components and a mixture of these components.
Figure 17:
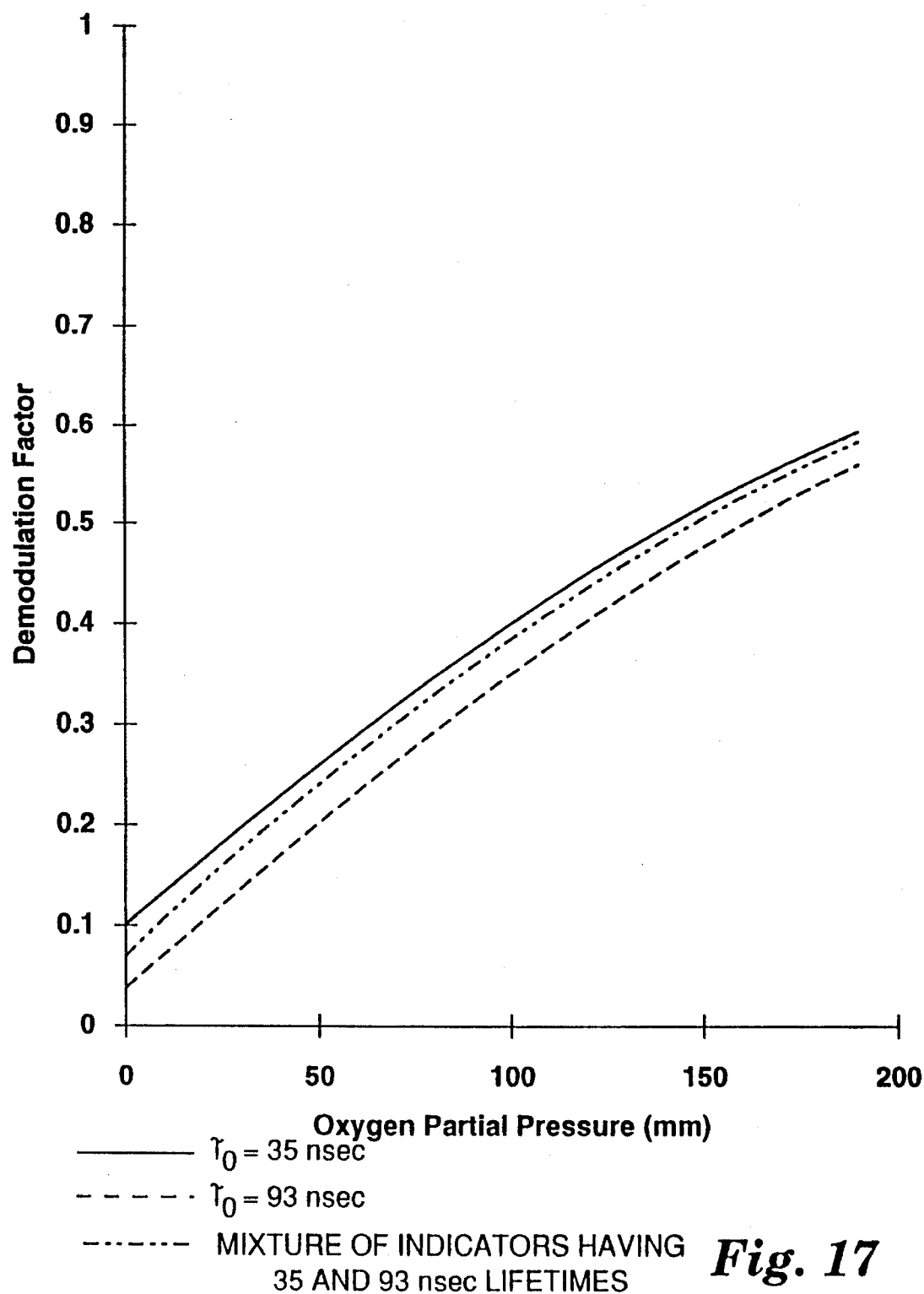

In contrast to conventional practice, the combination of high Stern-Volmer quenching constant and high modulation frequency are show in this example to provide calibration slopes that remain analyte sensitive and are insensitive to $\tau_o$ heterogeneity. FIGS. 16 and 17 are graphical representations of calculated calibration data of phase shift and demodulation factor (respectively) vs oxygen partial pressure for the VBP ($\tau_o$=35 nsec) and BP ($\tau_o$=93 nsec) monomeric indicator components described above in Example 1, and for a 50:50 mixture of these two monomeric indicator components. In contrast to conventional practice, the Stern-Volmer quenching constants have been increased by increasing the oxygen solubility and diffusivity, such that $ak_q$=9.5×10$^5$ mm$^{-1}$ sec$^{-1}$. Although FIGS. 16 and 17 are simulations with data points computed from the measured data described in Example 1, a sensing element having approximately this value of $ak_q$ can be achieved, for example, by dispersing the VBP and BP monomeric indicator components in a trimethylsilylpropyne matrix. Also in contrast to conventional practice, the product $\omega\tau_o$ has also been increased substantially by changing the modulation frequency from 3 to 45 MHz. The condition set forth in Equation 1 is therefore satisfied over the physiologically relevant range of oxygen partial pressures shown in FIGS. 16 and 17. For VBP in this sensor and over the physiological range of 40 to 120 mm: $\omega\tau_o$=9.9; $[[(k_q[Q])^2+\omega^2]\tau_o^2]/[1+2k_q\tau_o[Q]]$=27.2 to 12.7; and $k_q\tau_o[Q]$=1.33 to 4.00. For BP: $\omega\tau_o$=26.3; $[[(k_q[Q])^2+\omega^2]\tau_o^2]/[1+2k_q\tau_o[Q]]$=87.3 to 36.2; and $k_q\tau_o[Q]$=3.53 to 10.60.

Example 6

Figure 18:
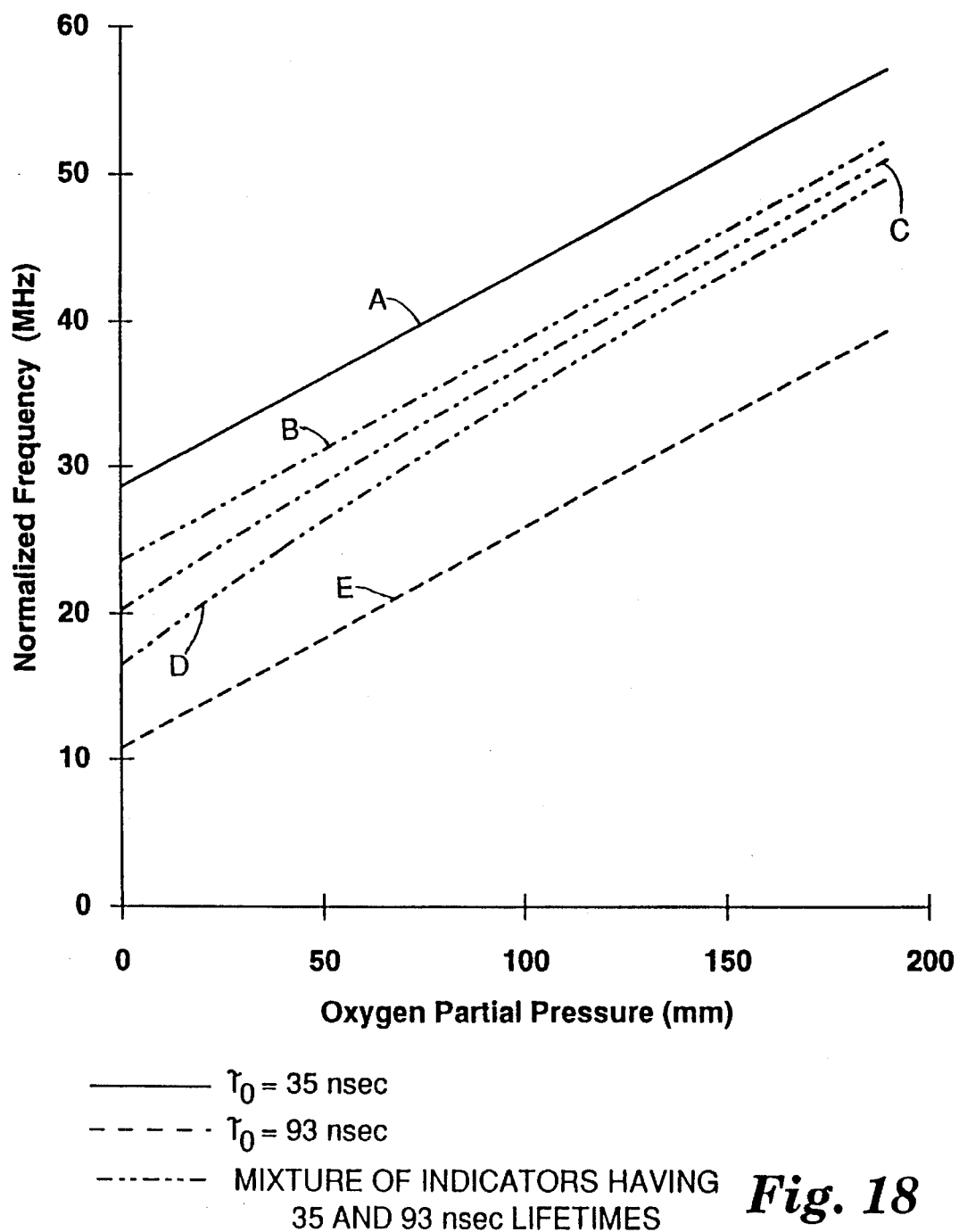
FIG. 18 is a graph illustrating calculated calibration data of phase-modulation mode 3 for two monomeric indicator components and a mixture of these components.

This example is also a simulation based on the calculations for the VBP, BP and 50:50 mixture indicator components described above in Example 4, again in a silicone matrix having oxygen solubility and diffusivity such that $ak_q$=1.5×10$^5$ mm$^{-1}$ sec$^{-1}$. Dispersions of these indicator components in a silicone matrix will have these characteristics. If the modulation frequency is allowed to vary such that the phase shift remains constant at $\Delta\Theta$=20°, 45° and 80°, (phase-modulation mode 3), calibration plots of the type shown in FIG. 18 are obtained. Based on the calibration relationship derived below for an individual fluorophore characterized by a single $\tau_o$, $f=(\tan\Theta/2\pi)[1/\tau_o+ak_q P_{O_2}]$.

For individual fluorophores with one $\tau_o$, the calibration curves are linear, and the calibration slopes become independent of $\tau_o$, depending only on the matrix dependent constants $ak_q$. In FIG. 18, calibration curves for the sensing elements with single fluorophores of $\tau_o$=35 nsec and $\tau_o$=93 nsec, shown by lines A and E, respectively, exhibit the same slope. If assurance can be made that a sensing element does not exhibit a bimodal distribution of $\tau_o$'s, then linear and constant calibration slopes can be assumed, and a single point calibration method can be established. However, in many cases, more than one $\tau_o$ is required to fully describe the fluorescence lifetime behavior of these sensing elements. In these cases, both the slopes and intercepts change. However, we have found that by going to large enough phase shifts, the slopes become independent of this heterogeneity, and single point calibration can be achieved. For example, FIG. 18 shows results for a 50:50 mixture of two non-interacting fluorophores, one with $\tau_{o1}$=35 nsec and the other with $\tau_{o2}$=93 nsec. Line B is for a phase shift of 80°, line C is for a phase shift of 45°; and line D is for a phase shift of 20°. As the phase shift is changed from 20 to 45 to 80 degrees, calibration slopes for the mixture become increasingly linear and the slopes approach that for the pure components. At $\Theta$=45 degrees, the calibration slope differs by 10% from that obtained for the pure components. At $\Theta$=80 degrees, calibration slopes for the mixture are linear and have the same slope as that of the pure components. This phase shift ensures sufficiently high modulation frequencies that the operating condition set forth in Equation 1 is met for all oxygen concentrations of interest. For VBP in this sensor and over the physiological range of 40 to 120 mm: $\omega\tau_o \geq 5.9$; $[[(k_q[Q])^2+\omega^2]\tau_o^2]/[1+2k_q\tau_o[Q]]$=24.8 to 34.3; and $k_q\tau_o[Q]$=0.211 to 0.634. For BP: $\omega\tau_o \geq 15.8$; $[[(k_q[Q])^2+\omega^2]\tau_o^2]/[1+2k_q\tau_o[Q]]$= 117 to 126; and $k_q\tau_o[Q]$= 0.56 to 1.69.

Note that in FIG. 18 the ordinate is entitled "Normalized Frequency (MHz)". For individual fluorophores with one $\tau_o$, $$\tan\theta=2\pi f\tau=(2\pi f\tau_o)/(1+ak_q\tau_o[O_2]).$$

Solving for f one obtains:

$$f=((1+ak_q\tau_o[O_2])/(2\pi\tau_o))\tan\theta.$$

Multiplying both sides of the above equality by the quantity $2\pi/\tan\theta$ one obtains:

$$2\pi f/\tan\theta=1/\tau_o+ak_q[O_2].$$

This latter equation is in the Stern/Volmer form, where the normalized frequency $2\pi f/\tan\theta$ equals $1/\tau$. Thus, for pure components the normalized frequency, $2\pi f/\tan\tau$, equals $1/\tau$.

Example 7

Figure 19:
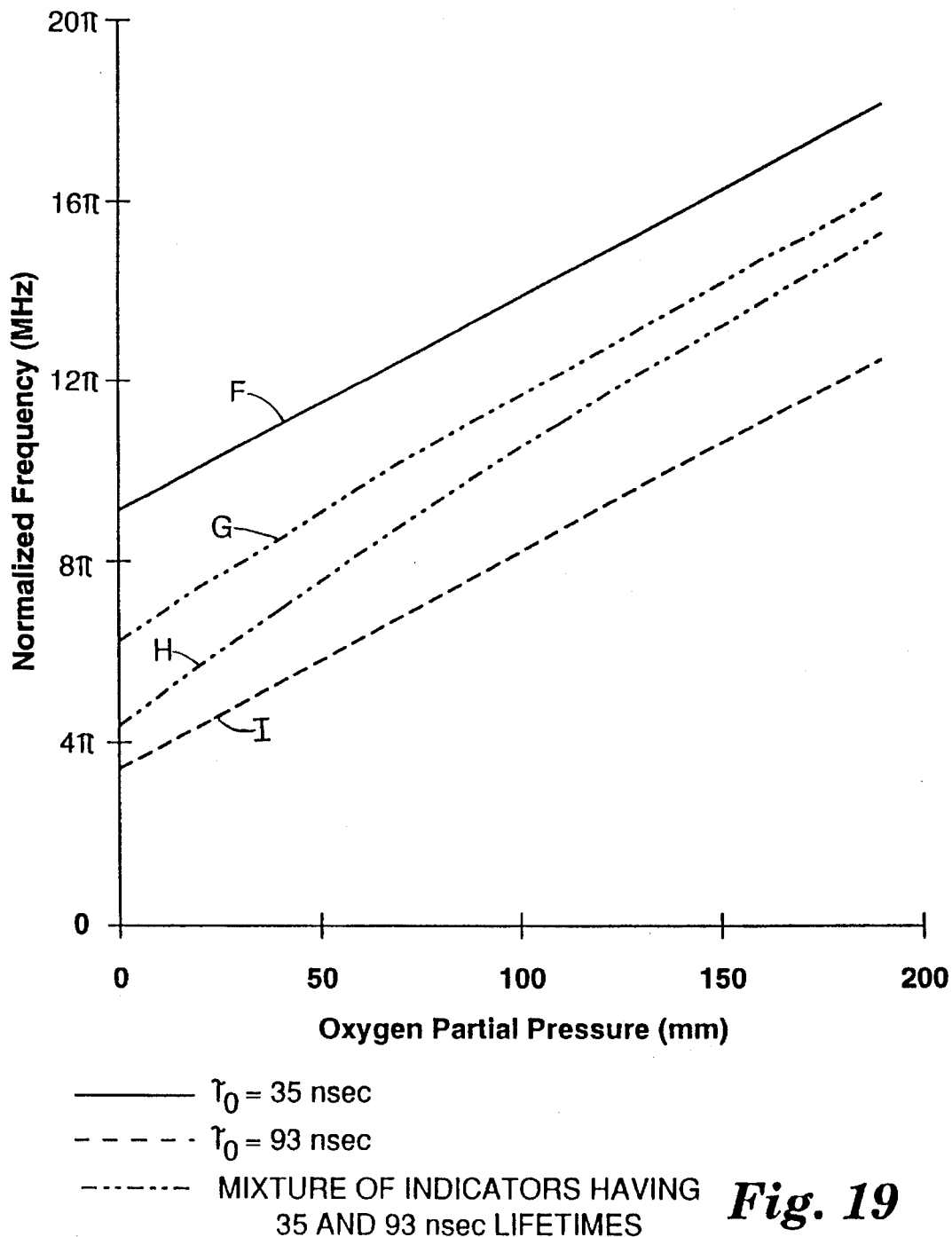
FIG. 19 is a graph illustrating calibration data of phase-modulation mode 4 for two monomeric indicator components and a mixture of these components.

In a manner similar to that described in Example 6 above, if the modulation frequency is allowed to vary such that the demodulation factor remains constant (phase-modulation mode 4) calibration plots of the type shown in FIG. 19 are obtained. The calibration relationship for an individual chromophor characterized by one $\tau_o$ is $f=((1/m)^2-1)^{1/2}[1/\tau_o+ak_qP_{O2}]$. As shown in FIG. 19, as the demodulation factor is changed from 0.9 (line "H") to 0.1 (line "G") calibration slopes for the mixture become increasingly linear and the slopes approach that for the pure components (lines "F" and "I"). At m=0.1, the calibration slope for the mixture is nearly linear and has nearly the same slope as that for the pure components. This demodulation factor ensures sufficiently high modulation frequencies that the operating condition set forth in Equation 1 is met for all oxygen concentrations of interest.

Note that in FIG. 19 the "Normalized Frequency (MHz)" can be similarly derived (as was done for FIG. 18) and for pure components equals $(2\pi f)/((1/m^2)-1)^{1/2}$.

Example 8

Figure 20:
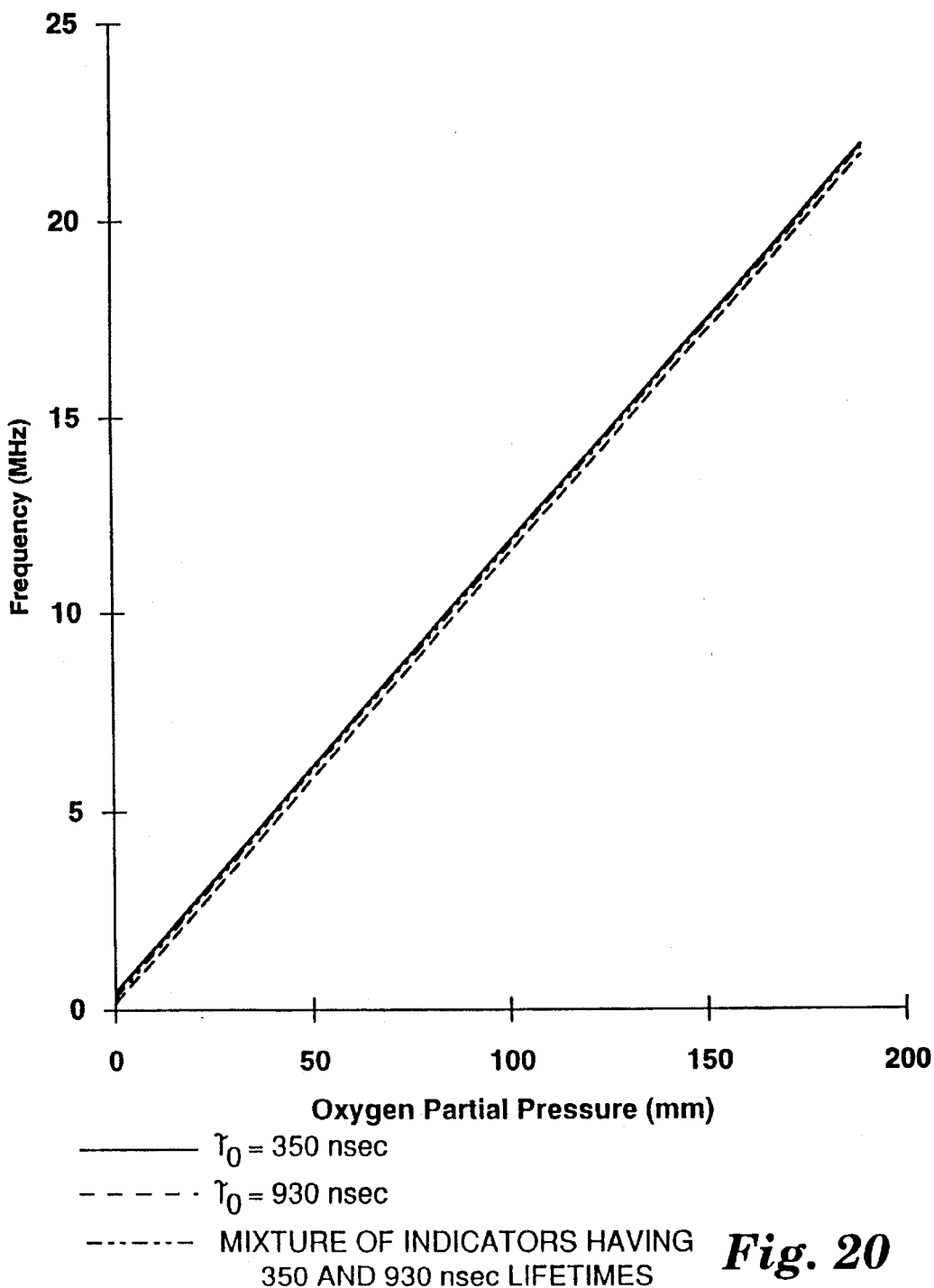
FIG. 20 is a calibration plot of frequency at constant phase shift (phase-modulation mode 3) as a function of the partial pressure of oxygen for two monomeric indicator components having relatively long lifetimes and a mixture of these components.
Figure 21:
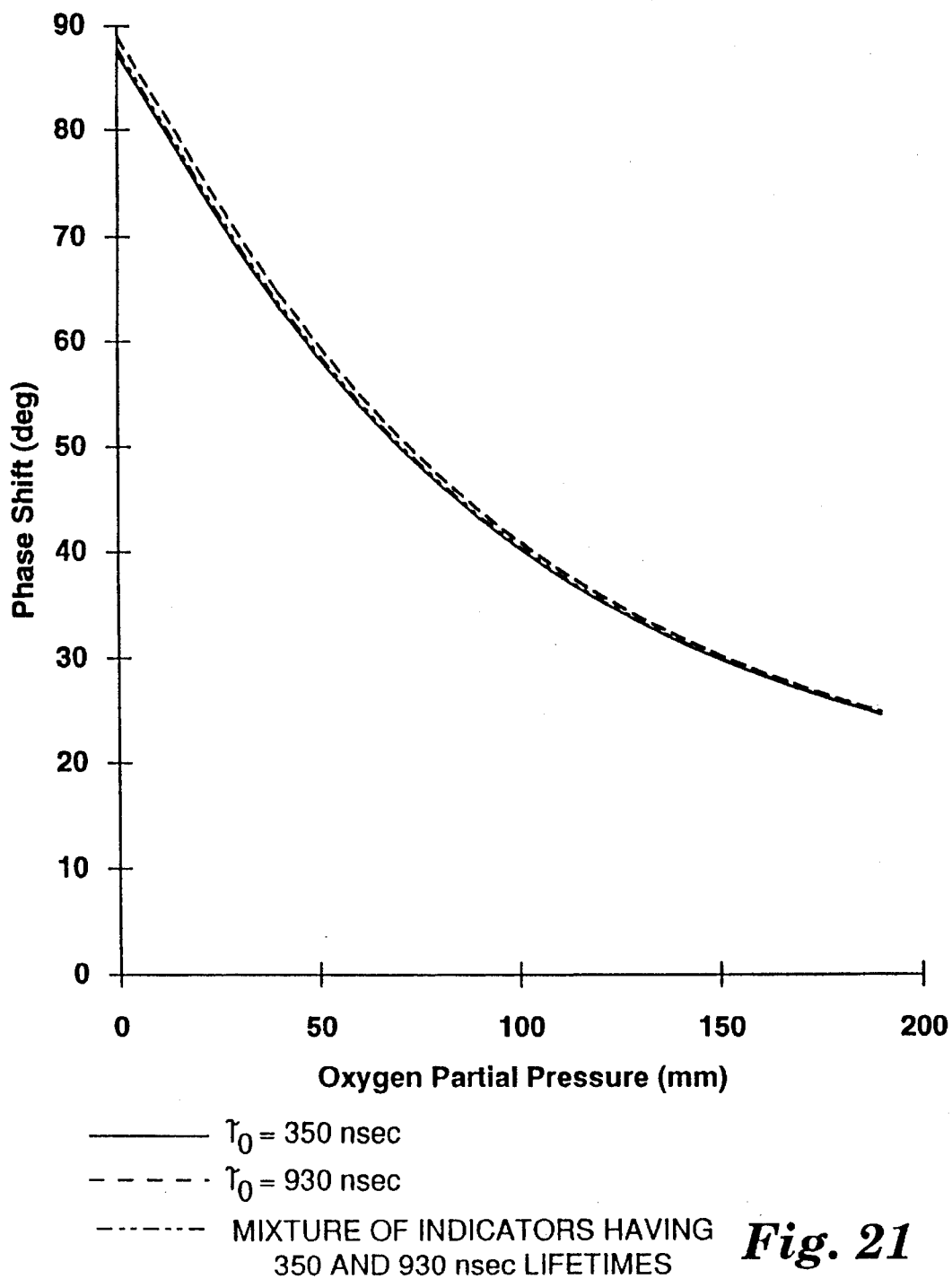
FIG. 21 is a calibration plot of phase shift at constant modulation frequency (phase-modulation mode 1) as a function of the partial pressure of oxygen for two monomeric indicator components having relatively long lifetimes and a mixture of these components.

FIGS. 20 and 21 are calibration plots of frequency at constant phase shift of 45° (mode 3) and phase shift at constant modulation frequency of 10 MHz (mode 1), respectively, as a function of the partial pressure of oxygen for dyes having lifetimes of 350 nsec and 930 nsec, and a 50:50 mixture of these dyes. The data lines shown in FIGS. 20 and 21 are simulations made by calculation, on the assumption the dyes are in a matrix for which $ak_q$=7.1×10$^5$ mm$^{-1}$sec$^{-1}$. Ruthenium dyes of the type disclosed generally in the Mauze et al. U.S. Pat. No. 5,057,277 can be made to have these relatively long lifetimes. These dyes can be dispersed in a trimethylsilylpropyne matrix to achieve an $ak_q$ of approximately 7.1×10$^5$ mm$^{-1}$ sec$^{-1}$. For the 350 nsec dye: $\omega\tau_o$=22.0; $[[(k_q[Q])^2+\omega^2]\tau_o^2]/[1+2k_q\tau_o[Q]]$= 27.91 to 22.65; and $k_q\tau_o[Q]$=9.94 to 29.82. For the 930 nsec dye; $\omega\tau_o$=58.4; $[[(k_q[Q])^2+\omega^2]\tau_o^2]/[1+2\ k_q\ \tau_o[Q]]$= 76.3 to 60.8; and $k_q\tau_o[Q]$=26.4 to 79.2. This example illustrates sensing instrument operation within the condition of Equation 1. With these relatively long lifetime dyes, the intercept of the calibration relationship, as well as the slope, is insensitive to $\tau_o$ variability. Even greater intercept insensitivity to $\tau_o$ variations may be obtained by using longer lifetime dyes in higher diffusivity matrices.

Figure 22:
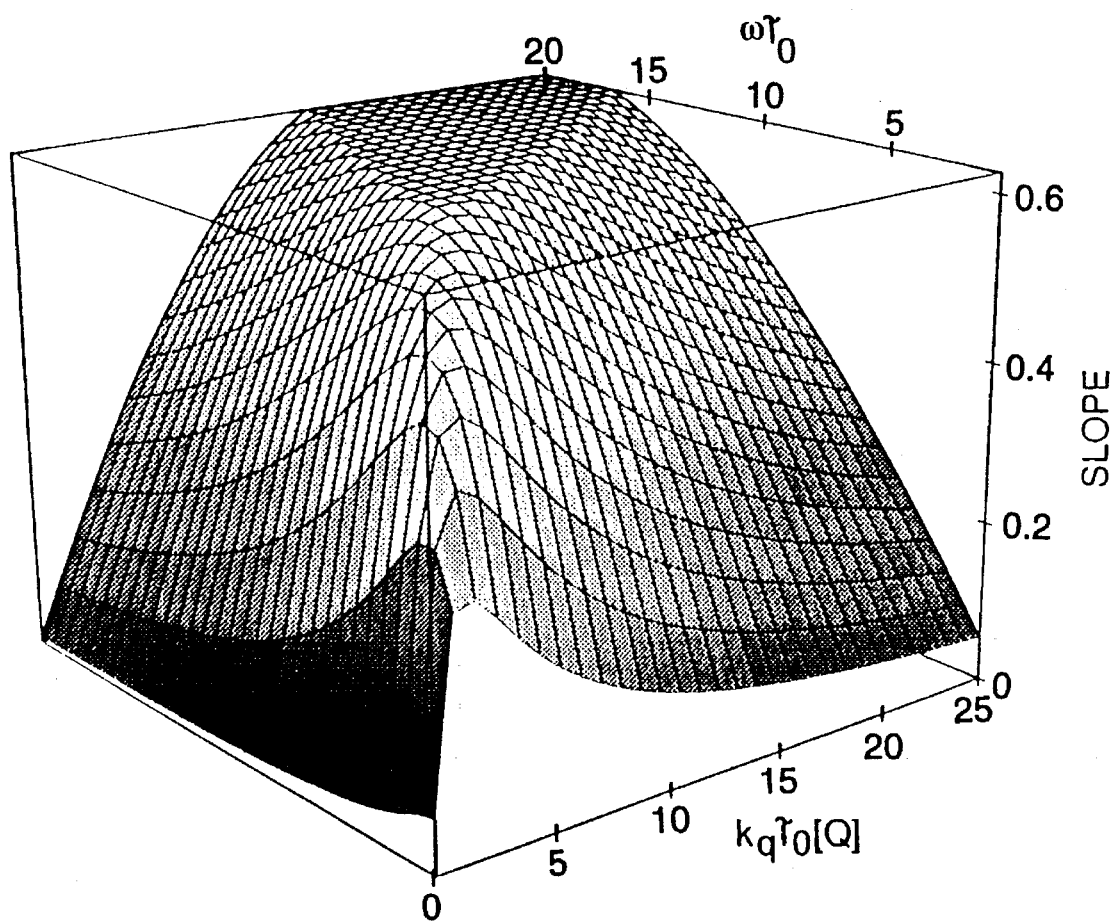
FIG. 22 is a three dimensional illustration of the calibration slope as a function of the quantities $\omega\tau_o$ and $k_q\tau_o[Q]$.

FIG. 22 is a three dimensional illustration of the calibration slope (degrees phase shift per mm oxygen partial pressure at 40 mm mercury) as a function of the quantities $\omega\tau_o$ and $k_q\tau_o[Q]$. This plot is truncated along the z-axis to illustrate a region of preferred operation: where the intercept of the calibration curve is independent of $\tau_o$ for all $\tau_o$ above $\tau_{oL}$; where the slope of the calibration curve is independent of $\tau_o$ for all $\tau_o$ above $\tau_{oL}$ (i.e., equation 1 is satisfied); and where the calibration slope is large. The intercept of the calibration curve becomes insensitive to $\tau_o$ variability when $1/\tau \gg 1/\tau_o$, or more quantitatively when $1/\tau > 10(1/\tau_o)$. This condition is satisfied when $k_q\tau_o[Q] > 9$.

CONCLUSION

The operating conditions set forth in Equation 1 provide for the use of unconventionally high modulation frequencies, unsuitable for accurate measurements of the excited state lifetime. However, in bypassing the explicit determination of the lifetime, as shown by phase-modulation modes 1–4, these high modulation frequencies enable accurate analyte concentration measurements to be made with sensing elements for which the Stern-Volmer quenching constant are considered too high for conventional practice. Also by operating under conditions set forth in Equation 1, calibration slopes, and slopes and intercepts, can be made independent of $\tau_o$ heterogeneity.

Although the present invention has been described with reference to preferred embodiments those skilled in the art will recognize that changes may be made in form and detail without departing from the spirit and scope of the invention.

What is claimed is:

1. An instrument for measuring the concentration of an analyte within an operating range of interest, comprising:
    a sensing element comprising a matrix material and an emissive indicator, wherein said matrix material is permeable to a quencher comprising said analyte or a substance related to said analyte by a known relationship, and wherein said emissive indicator has a bimolecular quenching rate constant $k_q$ for said quencher, one or more fluoresence liftimes $\tau_o$ above a lowest lifetime $\tau_{oL}$, and capable of emitting analyte concentration dependent signals having a concentration dependent parameter which varies as a function of analyte concentration when exposed to a excitation signal in the presence of quencher;

an excitation system coupled to the sensing element for providing the excitation signal at one or more radial frequencies $\omega$;

a detector coupled to the sensing element for detecting the analyte concentration dependent signal(s) and for providing detected signal(s);

a processor including memory for storing calibration information characterizing a relationship between analyte concentration and the first concentration dependent parameter, for univariantly processing the first detected signal(s) to derive the first concentration dependent parameter and providing output signal(s) representative of analyte concentration as a function of the derived concentration dependent parameter and the stored calibration information; and wherein the sensing element and excitation system are configured to enable the instrument to operate sufficiently within the operating condition where the quantity $\{[(k_q[Q])^2 + \omega^2]\tau_o^2\}$ is greater than 4 times the quantity $\{1+2k_q\tau_o[Q]\}$ for all analyte concentrations within the operating range of interest and for all lifetimes $\tau_o$ greater than $\tau_{oL}$, where [Q] is the concentration of said quencher in said matrix.

2. The instrument of claim 1, wherein the frequency of said excitation signal provides an operating condition where the quantity $\omega\tau_o$ is greater than 4 for all analyte concentrations within the operating range of interest and for all lifetimes $\tau_o$ greater than $\tau_{oL}$, and wherein said analyte and said quencher are oxygen.

3. The instrument of claim 1, wherein the frequency of said excitation signal provides an operating condition where the quantity $\omega\tau_o$ is greater than 6 for all analyte concentrations within the operating range of interest and for all lifetimes $\tau_o$ greater than $\tau_{oL}$, and wherein said matrix comprises a polymer.

4. The instrument of claim 1, wherein the sensing element is configured to provide an operating condition where the quantity $k_q\tau_o[Q]$ is greater than 10 for all analyte concentrations within the operating range of interest and for all lifetimes $\tau_o$ greater than $\tau_{oL}$.

5. The instrument of claim 1, wherein the sensing element is configured to provide an operating condition where the quantity $k_q\tau_o[Q]$ is greater than 15 for all analyte concentrations within the operating range of interest and for all lifetimes $\tau_o$ greater than $\tau_{oL}$, and wherein said analyte is selected from the group consisting of oxygen, ionized hydrogen, and carbon dioxide.

6. The instrument of claim 1, wherein the sensing element is configured to provide an operating condition where the quantity $k_q\tau_o[Q]$ is greater than 20 for all analyte concentrations within the operating range of interest and for all lifetimes $\tau_o$ greater than $\tau_{oL}$, and wherein said analyte and said quencher are oxygen.

7. The instrument of claim 1, wherein said concentration dependent parameter is the modulated frequency required to provide a constant phase shift or demodulation factor.

8. The instrument of claim 1, wherein the frequency of said excitation signal provides an operating condition where the quantity $\omega\tau_o$ is greater than 10 for all analyte concentrations within the operating range of interest and for all lifetimes $\tau_o$ greater than $\tau_{oL}$.

9. The instrument of claim 8, wherein said excitation system comprises a light source selected from the group consisting of light emitting diodes, laser diodes, frequency doubled laser diodes, and solid state light sources.

10. The instrument of claim 8, wherein said sensing element is configured to operate within the a-line circuit of an arterial catheter.

11. The instrument of claim 1, wherein the sensing element and excitation signal are configured so as to provide an operating condition where the quantity $\{[(k_q[Q])^2 + \omega^2]\tau_o^2\}$ is greater than 6 times the quantity $\{1+2k_q\tau_o[Q]\}$ for all analyte concentrations within the operating range of interest and for all lifetimes $\tau_o$ greater than $\tau_{oL}$, and wherein said matrix comprises a polymer.

12. The instrument of claim 11, wherein said excitation signal has a constant radial frequency $\omega_1$ and said sensing element emits analyte concentration dependent signals which are phase shifted by $\Delta\theta_1$ and demodulated by a demodulation factor $m_1$ with respect to said excitation signal, and wherein said processor univariantly processes said detected signals to derive the phase shift between said emitted signal and said excitation signal.

13. The instrument of claim 12, wherein said processor includes stored information characterizing a relationship between analyte concentration and the phase shift between one of said analyte concentration dependent signals and said excitation signal, univariantly processes the detected signal(s) to derive said phase shift, and provides output signal(s) representative of analyte concentration as a function of said stored information and said derived phase shift.

14. The instrument of claim 1, wherein the sensing element and excitation signal are configured so as to provide an operating condition where the quantity $\{[(k_q[Q])^2 + \omega^2]\tau_o^2\}$ is greater than 10 times the quantity $\{1+2k_q\tau_o[Q]\}$ for all analyte concentrations within the operating range of interest and for all lifetimes $\tau_o$ greater than $\tau_{oL}$.

15. The instrument of claim 14, wherein said emissive indicator comprises at least two monomeric components wherein at least one of said monomeric components is a monomeric indicator component and wherein said sensing element, when exposed to said excitation signal, provides a first emission signal from an unreacted first excited state and a second emission signal from a reacted second excited state complex produced in said sensing element from said monomeric components, and wherein said processor univariantly processes said first emitted signal or said second emitted signal or said first and second emitted signals to determine the concentration of said analyte.

16. The instrument of claim 15, wherein said processor includes stored information characterizing a relationship between analyte concentration and the phase shift difference between the first analyte concentration dependent signal and the second analyte concentration dependent signal, univariantly processes the detected signal(s) to derive said phase shift difference, and provides output signal(s) representative of analyte concentration as a function of said stored information and said derived phase shift difference.

17. An instrument for measuring the concentration of an analyte within an operating range of interest, comprising:

a sensing element comprising an emissive indicator configured for exposure to a quencher, said quencher comprising said analyte or a substance related to said analyte by a known relationship, and wherein said emissive indicator is characterized by a bimolecular quenching rate constant $k_q$ for said quencher, one or more fluoresence liftimes $\tau_o$ above a lowest lifetime $\tau_{oL}$, and capable of emitting analyte concentration dependent signals having a concentration dependent parameter which varies as a function of analyte concentration when exposed to a excitation signal in the presence of quencher;

an excitation system coupled to the sensing element for providing the excitation signal at one or more radial frequencies $\omega$;

a detector coupled to the sensing element for detecting the analyte concentration dependent signal(s) and for providing detected signal(s);

a processor including memory for storing calibration information characterizing a relationship between analyte concentration and the concentration dependent parameter, for univariantly processing the detected signal(s) to derive the concentration dependent parameter and providing output signal(s) representative of analyte concentration as a function of the derived concentration dependent parameter and the stored calibration information; and wherein the sensing element and excitation system are configured to enable the instrument to operate sufficiently within the operating condition where the quantity $\{[(k_q[Q])^2+\omega^2]\tau_o^2\}$ is sufficiently greater than the quantity $\{1+2k_q\tau_o[Q]\}$ such that a slope of the relationship between the concentration dependent parameter and analyte concentration is independent of $\tau_o$ variability for all analyte concentrations within the operating range of interest and for all lifetimes $\tau_o$ greater than $\tau_{oL}$, where [Q] is the concentration of said quencher in said sensing element.

18. The instrument of claim 17, wherein said analyte is selected from the group consisting of oxygen, ionized hydrogen, and carbon dioxide.

19. An instrument for measuring the concentration of oxygen within an operating range of interest, comprising:

a sensing element comprising a matrix material having an oxygen solubility constant a, and an emissive indicator, wherein said matrix material is permeable to oxygen, and wherein said emissive indicator has a bimolecular quenching rate constant $k_q$ for oxygen, one or more fluoresence liftimes $\tau_o$ above a lowest lifetime $\tau_{oL}$, and capable of emitting oxygen concentration dependent signals having a concentration dependent parameter which varies as a function of oxygen concentration when exposed to a excitation signal in the presence of quencher;

an excitation system coupled to the sensing element for providing the excitation signal at one or more radial frequencies $\omega$;

a detector coupled to the sensing element for detecting the oxygen concentration dependent signal(s) and for providing detected signal(s);

a processor including memory for storing calibration information characterizing a relationship between oxygen concentration and the first concentration dependent parameter, for univariantly processing the first detected signal(s) to derive the first concentration dependent parameter and providing output signal(s) representative of oxygen concentration as a function of the derived concentration dependent parameter and the stored calibration information; and wherein the sensing element and excitation system are configured to enable the instrument to operate sufficiently within the operating condition where the quantity $\{[(ak_qP_{o2})^2+\omega^2]\tau o^2\}$ is greater than 4 times the quantity $\{1+2ak_q\tau_oP_{o2}\}$ for all oxygen concentrations within the operating range of 40 to 200 mm Hg and for all lifetimes τo greater than τoL.

20. The instrument of claim 19, wherein said sensing element and said excitation signal are configured so as to provide an operating condition where the quantity $\{[(ak_qP_{o2})^2+\omega^2]\tau_o^2\}$ is greater than 6 times the quantity $(1+2ak_q\tau_oP_{o2})$ for all oxygen partial pressures within the operating range of 40 to 120 mm Hg and for all lifetimes $\tau_o$ greater than $\tau_{oL}$.

21. The instrument of claim 19, wherein said oxygen permeable matrix comprises a silicone polymer and said emissive indicator comprises a polyaromatic hydrocarbon.

22. The instrument of claim 19, wherein said emissive indicator comprises at least two monomeric components wherein at least one of said monomeric components is a monomeric indicator component and wherein said sensing element, when exposed to said excitation signal, provides a first emission signal from an unreacted first excited state and a second emission signal from a reacted second excited state complex produced in said sensing element from said monomeric components, and wherein said first emitted signal or said second emitted signal or said first and second emitted signals are univariantly processed to determine the concentration of said analyte.

23. The instrument of claim 19, wherein the frequency of said excitation signal provides an operating condition where the quantity $\omega\tau_o$ is greater than 10 for all oxygen concentrations within the operating range of 40 to 200 mm Hg and for all lifetimes $\tau_o$ greater than $\tau_{oL}$.

24. The instrument of claim 19, wherein the sensing element is configured to provide an operating condition where the quantity $ak_q\tau_oP_{o2}$ is greater than 10 for all oxygen concentrations within the operating range of 40 to 200 mm Hg and for all lifetimes $\tau_o$ greater than $\tau_{oL}$.

25. The instrument of claim 19, wherein said excitation signal has a constant radial frequency $\omega_1$ and said sensing element emits analyte concentration dependent signals which are phase shifted by $\Delta\theta_1$ and demodulated by a demodulation factor $m_1$ with respect to said excitation signal, and wherein said processor univariantly processes said detected signals to derive the phase shift between said emitted signal and said excitation signal.

26. The instrument of claim 19, wherein said medium is blood.

27. The instrument of claim 19, wherein said sensing element and said excitation signal are configured so as to provide an operating condition where the quantity $\{[(ak_qP_{o2})^2+\omega^2]\tau_o^2\}$ is greater than 10 times the quantity $\{1+2ak_q\tau_oP_{o2}\}$ such that a slope of the relationship between the concentration dependent parameter and oxygen partial pressure is independent of $\tau_o$ variability or heterogeneity or both for all oxygen partial pressures within the operating range of 40 to 200 mm Hg and for all lifetimes $\tau_o$ greater than $\tau_{oL}$.

28. The instrument of claim 27, wherein the sensing element is configured to provide an operating condition where the quantity $ak_q\tau_oP_{o2}$ is greater than 10 such that the intercept of the relationship between the concentration dependent parameter and oxygen partial pressure is independent of $\tau_o$ variability or heterogeneity or both.

* * * * *

UNITED STATES PATENT AND TRADEMARK OFFICE
CERTIFICATE OF CORRECTION

PATENT NO.: 5,518,694

DATED: May 21, 1996

INVENTOR(S): James G. Bentsen

It is certified that error appears in the above-identified patent and that said Letters Patent is hereby corrected as shown below:

Col. 17, line 56, "$k_q\omega_o$" should read -- $k_q\tau_o$ --.

Col. 20, Table 3a, under column titled "% $O_2$," "10.37" should read -- 10.35 --.

Signed and Sealed this

Ninth Day of December, 1997

Attest:

BRUCE LEHMAN

Attesting Officer

Commissioner of Patents and Trademarks